United States Patent
Altendorf

(10) Patent No.: US 9,329,026 B2
(45) Date of Patent: May 3, 2016

(54) HOLE-MEASUREMENT SYSTEMS AND METHODS USING A NON-ROTATING CHROMATIC POINT SENSOR (CPS) PEN

(71) Applicant: Mitutoyo Corporation, Kanagawa-ken (JP)

(72) Inventor: Eric Herbert Altendorf, Everett, WA (US)

(73) Assignee: Mitutoyo Corporation, Kanagawa-ken (JP)

(*) Notice: Subject to any disclaimer, the term of this patent is extended or adjusted under 35 U.S.C. 154(b) by 89 days.

(21) Appl. No.: 14/099,790

(22) Filed: Dec. 6, 2013

(65) Prior Publication Data

US 2015/0159998 A1    Jun. 11, 2015

(51) Int. Cl.
| | |
|---|---|
| *G01B 11/02* | (2006.01) |
| *G01B 11/08* | (2006.01) |
| *G01B 11/00* | (2006.01) |
| *G01B 11/14* | (2006.01) |
| *G01B 11/12* | (2006.01) |
| *G01N 21/954* | (2006.01) |

(52) U.S. Cl.
CPC .............. *G01B 11/08* (2013.01); *G01B 11/005* (2013.01); *G01B 11/026* (2013.01); *G01B 11/12* (2013.01); *G01B 11/14* (2013.01); *G01N 21/954* (2013.01); *G01B 2210/50* (2013.01)

(58) Field of Classification Search
CPC ........... G01J 1/00; G01N 21/88; G01B 11/00; G01B 5/25; G01B 9/02
See application file for complete search history.

(56) References Cited

U.S. PATENT DOCUMENTS

| | | | | |
|---|---|---|---|---|
| 4,539,753 | A * | 9/1985 | Fitzpatrick | ...................... 33/520 |
| 7,477,401 | B2 | 1/2009 | Marx et al. | |

(Continued)

OTHER PUBLICATIONS

Molesini et al., "Pseudocolor effects of longitudinal chromatic aberration," Journal of Optics, 17(6):279-282, 1986.

*Primary Examiner* — Tarifur Chowdhury
*Assistant Examiner* — Jamil Ahmed
(74) *Attorney, Agent, or Firm* — Seed IP Law Group PLLC

(57) ABSTRACT

A chromatic confocal point sensor (CPS) system and associated methods are provided for measuring holes. A CPS optical pen includes a beam dividing deflecting element that directs measurement light simultaneously along at least three directions to the interior surface of the hole. A CPS electronics portion comprises a light generator, a spectrometer, and a signal processor. In operation, the CPS pen directs measurement light to the interior surface along the at least three directions, and the spectrometer receives measurement light reflected from those directions back through the pen and provides a spectral intensity profile comprising spectral peak components corresponding to distances to the interior surface along those directions. The hole characteristic may be determined based at least partially on those distances. The CPS pen may be used as a probe on a coordinate measuring machine (CMM). The CPS pen does not require rotation in a hole to measure the hole.

20 Claims, 14 Drawing Sheets

(56) References Cited

U.S. PATENT DOCUMENTS

| | | |
|---|---|---|
| 7,626,705 B2 | 12/2009 | Altendorf |
| 7,876,456 B2 | 1/2011 | Sesko |
| 7,990,522 B2 | 8/2011 | Sesko |
| 8,194,251 B2 | 6/2012 | Emtman et al. |
| 2006/0215176 A1* | 9/2006 | Van Coppenolle et al. ... 356/603 |
| 2007/0086000 A1* | 4/2007 | Messerschmidt et al. . 356/241.1 |
| 2008/0024793 A1* | 1/2008 | Gladnick ...................... 356/603 |
| 2009/0028910 A1* | 1/2009 | DeSimone et al. ........... 424/401 |
| 2009/0165317 A1* | 7/2009 | Little ............................... 33/503 |
| 2010/0027028 A1* | 2/2010 | Kuriyama .......... G01B 9/02022 356/495 |
| 2012/0050723 A1* | 3/2012 | Emtman et al. ................ 356/123 |
| 2012/0180590 A1* | 7/2012 | Meisman ................... 74/479.01 |

\* cited by examiner

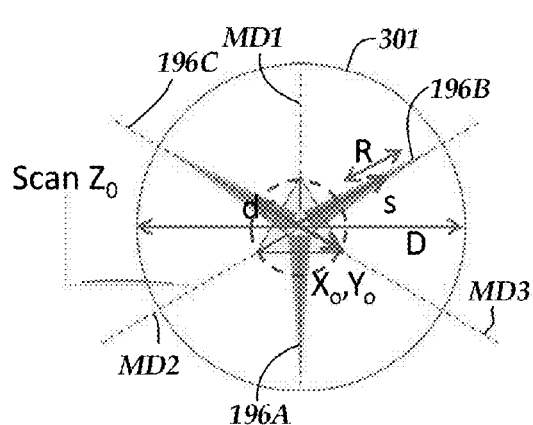
*Fig.10A.*
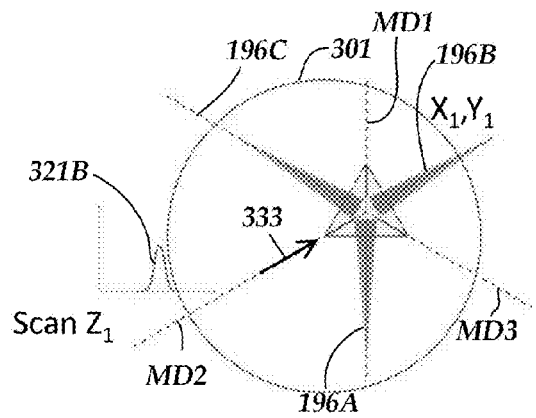
*Fig.10B.*
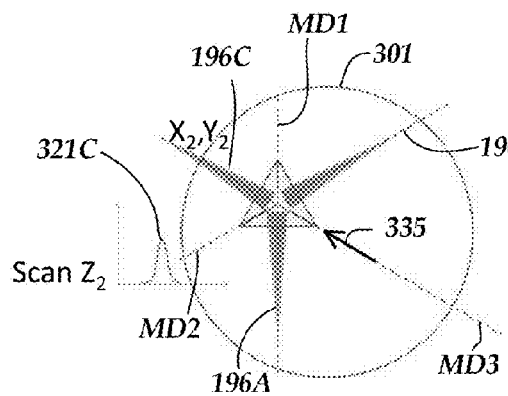
*Fig.10C.*
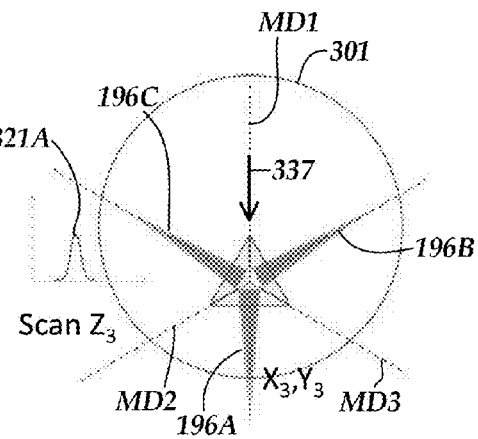
*Fig.10D.*
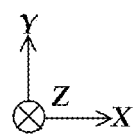

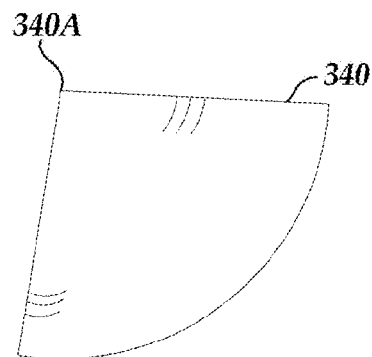
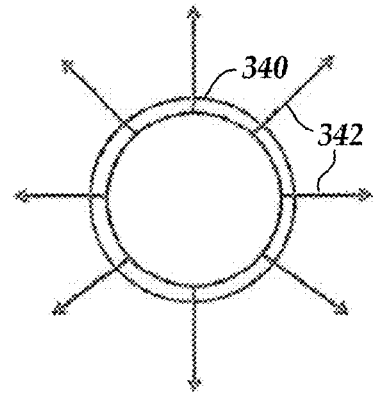
*Fig.15A.*  *Fig.15B.*
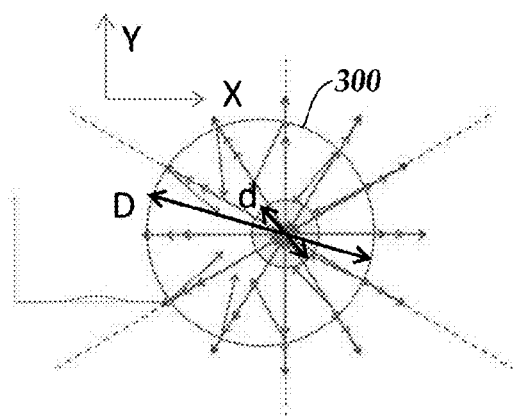
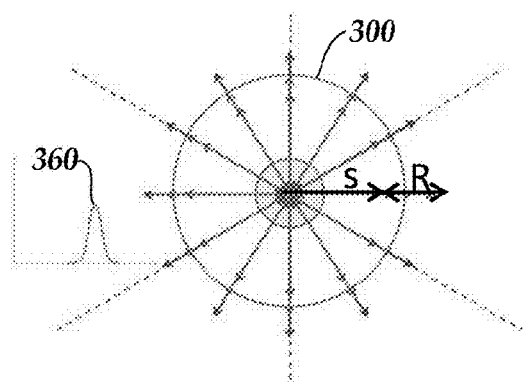
*Fig.16A.*  *Fig.16B.*

HOLE-MEASUREMENT SYSTEMS AND METHODS USING A NON-ROTATING CHROMATIC POINT SENSOR (CPS) PEN

BACKGROUND

1. Technical Field

The invention relates generally to precision measurement instruments, and more particularly to systems and methods for operating a chromatic point sensor (CPS) pen to measure a characteristic of a hole, such as a hole diameter or the like, without having to rotate the CPS pen.

2. Description of the Related Art

Axial chromatic aberration techniques may be utilized for distance sensing metrology. As described in "Pseudocolor Effects of Longitudinal Chromatic Aberration", G. Molesini and S. Quercioli, J. Optics (Paris), 1986, Volume 17, No. 6, pages 279-282, controlled longitudinal chromatic aberration (also referred to herein as axial chromatic dispersion) may be introduced in an optical imaging system, causing the imaging system focal length to vary with wavelength, which provides means for optical metrology. In particular, a lens can be designed whose back focal length (BFL) is a monotonic function of wavelength. In white light operation, such a lens exhibits a rainbow of axially dispersed foci that can be used as a spectral probe for distance sensing applications.

As a further example, U.S. Pat. No. 7,477,401, which is incorporated herein by reference in its entirety, discloses that an optical element having axial chromatic aberration may be used to focus a broadband light source such that the axial distance or height of a surface determines which wavelength is best focused at that surface. Upon reflection from the surface, the light is refocused onto a small detector aperture, such as a pinhole and/or the end of an optical fiber, and only the wavelength that is well-focused on the surface is well-focused on the aperture. Other wavelengths are poorly focused and will not couple much power into the aperture. A spectrometer measures the signal level for each wavelength returned through the aperture. A wavelength intensity peak effectively indicates the distance or height of the surface.

Certain manufacturers refer to a practical and compact optical assembly that is suitable for chromatic confocal ranging in an industrial setting as a chromatic confocal point sensor, a chromatic point sensor (CPS) including an optical pen and/or as simply an "optical pen." One example of optical pen instruments that measure Z height are those manufactured by STIL, S.A. of Aix-en-Provence, France (STIL S.A.). As a specific example, the STIL optical pen model number OP 300NL measures Z heights and has a 300 micron range.

Another configuration for a chromatic confocal point sensor is described in commonly assigned U.S. Pat. No. 7,626,705, which is hereby incorporated herein by reference in its entirety. This patent discloses a lens configuration providing an improved optical throughput and an improved spot size, which results in improved measurement resolution in comparison with various commercially available configurations.

Applications of currently available optical pens to measure characteristics of a hole, such as a hole diameter, require rotating the optical pen relative to the hole to be measured in order to measure different portions of the hole wall and determine its overall shape and/or location. Pen rotation requires complex opto-mechanical parts to effect the rotation. In various applications, rotation of the pen is time-consuming and lowers measurement throughput. Also, rotation of the pen inevitably introduces some level of runout and/or wobble and related measurement errors.

Commonly assigned U.S. Pat. No. 8,194,251 ("the '251 patent"), which is incorporated herein by reference in its entirety, discloses a dual beam optical pen which may be positioned to measure two surface regions simultaneously. Generally speaking, while the dual beam configurations disclosed in the '251 patent may provide certain advantages relative to single beam optical pens, the pens in the '251 patent are not specifically configured for reliable and efficient hole measurement, particularly for measuring hole diameters that may approach the pen diameter.

For various applications involving measurement of holes and/or their interior surfaces, improvements in the configuration of and method of using CPS optical pens may be desirable. The present invention is directed to providing systems and methods for operating a CPS optical pen to measure a characteristic of the interior surfaces of a hole, such as a hole diameter, without having to rotate the pen.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

According to various exemplary embodiments of the present invention, a method is provided for using a chromatic point sensor (CPS) system to inspect a geometric characteristic of a hole that is at least partially surrounded by an interior surface. The method includes generally five steps. The first step is to provide a CPS system, which includes an electronics portion and an optical pen. The electronics portion includes a source light generating portion, a spectrometer, and a signal processor. The optical pen includes a housing that extends along a central Z axis of the optical pen, a confocal aperture that outputs source light, an axial chromatic aberration portion arranged to input the source light and output measurement light that is focused with axial chromatic aberration, and a beam dividing deflecting element arranged to distribute the measurement light simultaneously along at least three measurement directions transverse to the central Z axis. For example, the beam dividing deflecting element may be a pyramid shaped reflective optical element including at least three planar reflective facets corresponding to the at least three measurement directions, or a cone-shaped reflective optical element. The second step is to position the optical pen at a position inside the hole such that the measurement light is incident on the interior surface along the at least three measurement directions. The third step is to receive the measurement light, which is reflected from the at least three measurement directions back through the confocal aperture of the optical pen at the position. The fourth step is to operate the CPS system to obtain a spectral intensity profile of the measurement light. The spectral intensity profile includes spectral peak components corresponding to distances to the interior surface that are within the optical pen's measuring range along the at least three measurement directions. The fifth step is to determine the geometric characteristic of the hole, such as the hole diameter and the like, based at least partially on signal processing operations that include analyzing the spectral intensity profile to determine at least a first distance measurement from the optical pen to the interior surface along at least a first measurement diameter.

In some exemplary embodiments, the hole has a circular cross-section. The hole has a radius r and the method may include configuring or selecting the optical pen such that its measuring range along each of the at least three measurement directions extends at least a distance RMAX' from its central Z axis, wherein RMAX'>r.

In some embodiments, the step of positioning the optical pen at the position includes positioning the optical pen approximately centered in the hole such that all the spectral peak components in the spectral intensity profile substantially coincide to form a combined spectral peak indicative of an average radius of the interior surface along the at least three measurement directions.

In further aspects of the invention, the optical pen is coupled to a coordinate measuring machine (CMM), and the CMM is used to position the optical pen. The location of the center of the hole may be determined based on CMM coordinates corresponding to the position.

In some embodiments, the step of positioning the optical pen at the position in the hole includes positioning the optical pen at a position that provides the highest or narrowest combined spectral peak among those obtained at a plurality of positions in the hole. The highest or narrowest combined spectral peak may indicate an average radius of the hole, for example.

In other embodiments, the step of positioning the optical pen at the position in the hole includes positioning the optical pen off center in the hole such that at least three spectral peak components in the spectral intensity profile are isolated spectral peak components respectively corresponding to the distances from the optical pen to the interior surface along the at least three measurement directions. For example, an angular direction/orientation of each of the at least three measurement directions relative to the hole center may be inferred from the direction/orientation of the off center position relative to the hole center.

In still other embodiments, the step of positioning the optical pen at the position in the hole includes positioning the optical pen at a first off center position in the hole such that at least a first spectral peak component in the spectral intensity profile is an isolated spectral peak component corresponding to a unique distance from the optical pen to the interior surface along a corresponding unique measurement direction at the first off center position. Further, when the optical pen is coupled to a coordinate measuring machine (CMM), the CMM is used to position the optical pen, and the method additionally includes repeating the positioning, receiving, and operating steps corresponding to second and third off center positions such that at least second and third isolated spectral peak components in second and third spectral intensity profiles are obtained as isolated spectral peak components respectively corresponding to unique distances from the optical pen to the interior surface along corresponding unique measurement directions at the second and third off center positions. Then, in the step of determining the geometric characteristic, the signal processing operations include: (a) analyzing at least the first, second and third spectral intensity profiles to determine at least first, second and third distance measurements from the optical pen to the interior surface along the corresponding unique measurement directions at the first, second and third off center positions, and (b) determining the geometric characteristic of the hole based on at least the first, second and third distance measurements and CMM coordinates respectively corresponding to the first, second and third off center positions.

In some aspects of the invention, the interior surface of the hole includes screw threads, and the optical pen is coupled to a CMM which is used to position the optical pen. The step of positioning the optical pen at the position in the hole includes positioning the optical pen at a current position, which corresponds to an axial position along a direction parallel to a central axis of the hole and a current off center position transverse to the central axis of the hole, such that at least a first spectral peak component in the corresponding spectral intensity profile is an isolated spectral peak component corresponding to a unique distance from the optical pen to the interior surface along a corresponding unique measurement direction at the current position. The method further includes repeating the positioning, receiving, and operating steps at a plurality of different current positions that correspond to a plurality of different axial positions (along Z axis). In the step of determining the geometric characteristic, the signal processing operations include: (a) analyzing a plurality of spectral intensity profiles, respectively corresponding to the plurality of different current positions corresponding to the plurality of different axial positions, to determine a plurality of distance measurements from the optical pen to the screw threads along a corresponding unique measurement direction at the plurality of different current positions that correspond to the plurality of different axial positions, and (b) determining the geometric characteristic of the screw threads based on at least some of the plurality of distance measurements at the plurality of different current positions that correspond to the plurality of different axial positions.

According to further exemplary embodiments of the present invention, a chromatic confocal point sensor (CPS) system is provided for inspecting a geometric characteristic of a hole that is at least partially surrounded by an interior surface. The CPS system includes an optical pen comprising a housing that extends along a central Z axis of the optical pen, a confocal aperture that outputs source light, an axial chromatic aberration portion arranged to input the source light and output measurement light that is focused with axial chromatic aberration, and a beam dividing deflecting element arranged to distribute the measurement light simultaneously along at least three measurement directions transverse to the central Z axis. The CPS system further includes an electronics portion comprising a source light generating portion, a spectrometer, and a signal processor. The electronics portion is configured such that: (i) when the optical pen is positioned at a position inside the hole, the electronics portion operates such that the measurement light is incident on the interior surface along the at least three measurement directions, and the spectrometer receives the measurement light reflected from the at least three measurement directions back through the confocal aperture of the optical pen at the position; (ii) the signal processor operates in conjunction with the spectrometer to obtain a spectral intensity profile of the measurement light, wherein the spectral intensity profile comprises spectral peak components corresponding to distances to the interior surface that are within the optical pen's measuring range along the at least three measurement directions; and (iii) the signal processor performs the operations comprising at least one of a), b) and c) as follows:

a) determining the geometric characteristic of the hole based at least partially on signal processing operations comprising analyzing the spectral intensity profile to determine at least a first distance measurement from the optical pen to the interior surface along at least a first measurement direction;

b) analyzing the spectral intensity profile to determine at least a first distance measurement from the optical pen to the interior surface along at least a first measurement direction, and outputting the at least first distance measurement to an external system configured to determine the geometric characteristic of the hole based at least partially on the at least first distance measurement; and c) outputting the spectral intensity profile to an external system configured to determine the geometric characteristic of the hole based at least partially on signal processing operations comprising analyzing the spectral intensity profile to determine at least a first distance measurement from the optical pen to the interior surface along at least a first measurement direction.

In various exemplary embodiments, the external system is a CMM to which the optical pen is coupled, wherein the CMM is configured to control position and movement of the optical pen. In some embodiments, the CMM is configured to: (a) automatically position the optical pen at the position inside a hole located on a workpiece to be inspected by the CMM, wherein the position is a predetermined position defined in a part program executed by the CMM; and (b) determine the geometric characteristic of the hole based at least partially on the at least first distance measurement in combination with CMM coordinates corresponding to the predetermined position.

BRIEF DESCRIPTION OF THE SEVERAL VIEWS OF THE DRAWINGS

FIG. 3 is a cross-sectional view of a hole with screw threads, in which a conventional optical pen may be inserted and rotated to measure a geometric characteristic of the hole such as the hole diameter, thread heights, and the like.

FIGS. 10A-10D schematically illustrate a method of operating a CPS optical pen to inspect a geometric characteristic of a hole, without having to rotate the optical pen, according to some embodiments of the present invention.

FIG. 15A illustrates a cone-shaped reflective optical element that may be used as a beam dividing deflecting element according to some embodiments of the present invention, and FIG. 15B illustrates a cone disk of measurement light that may be produced by the cone-shaped reflective optical element of FIG. 15A.

FIGS. 16A and 16B schematically illustrate a further method of operating a CPS optical pen, which may include the cone-shaped reflective optical element at its distal end, to inspect a radius of a hole, without having to rotate the optical pen, according to some embodiments of the present invention.

DETAILED DESCRIPTION

Figure 1:
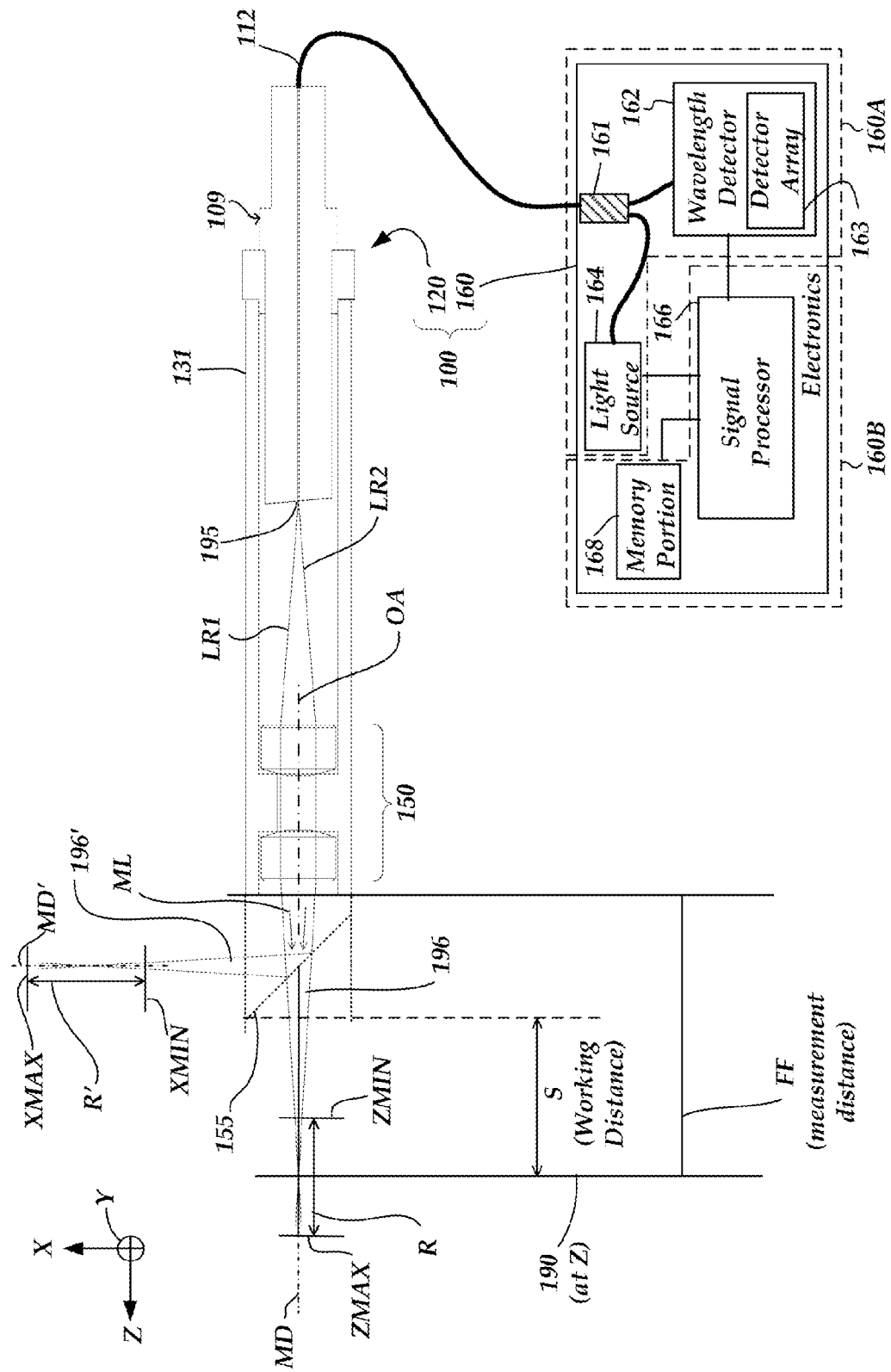
FIG. 1 is a block diagram of an exemplary chromatic point sensor (CPS) including an optical pen that outputs measurement light.

FIG. 1 is a block diagram of an exemplary chromatic confocal point sensor or a chromatic point sensor (CPS) 100. The chromatic confocal point sensor 100 has certain similarities to sensors described in U.S. Pat. Nos. 7,876,456; 7,990,522; and 8,194,251, which are incorporated herein by reference in their entirety. As shown in FIG. 1, the chromatic confocal point sensor 100 includes an optical pen 120 and an electronics portion 160. The optical pen 120 includes a fiber optic connector 109, a housing 131 that extends along a central Z axis of the optical pen 120, and an axial chromatic aberration portion 150. As illustrated, the fiber optic connector 109 is attached to the end of the housing 131, and receives an in/out optical fiber (not shown in detail) encased in a fiber optic cable 112 extending from the electronics portion 160. The in/out optical fiber outputs source light from a light source 164 (in the electronics portion 160) through a fiber confocal aperture 195, and receives reflected measurement light also through the fiber confocal aperture 195.

In operation, the axial chromatic aberration portion 150, which includes a lens or lenses that provide an axial chromatic aberration (dispersion), inputs (receives) broadband (e.g., white) source light emitted from the fiber end through the fiber confocal aperture 195, and outputs measurement light focused with axial chromatic aberration. As a result, the focal point of the measurement light along the optical axis OA (which coincides with the measurement direction MD in FIG. 1) is at different distances depending on the wavelength of the light, as is known for chromatic confocal sensor systems. The measurement light includes a wavelength that is focused on a workpiece surface 190 at a position Z, which is at the measurement distance (FF) relative to the optical pen 120. Upon reflection from the workpiece surface 190, reflected measurement light is refocused by the axial chromatic aberration portion 150 onto the fiber confocal aperture 195. The operative source light and measurement light are bounded by the limiting rays LR1 and LR2. Due to the axial chromatic aberration, only one wavelength will have a front focus dimension FF that matches the measurement distance from the optical pen 120 to the surface 190. The optical pen is configured such that the wavelength that is best focused at the surface 190 will also be the wavelength of the reflected measurement light that is best focused at the fiber confocal aperture 195. The fiber confocal aperture 195 spatially filters the reflected measurement light such that predominantly the best focused wavelength passes through the fiber confocal aperture 195 and into the core of the optical fiber cable 112. The optical fiber cable 112 routes the reflected measurement light to a wavelength detector 162 configured to determine the wavelength having the dominant intensity, which corresponds to the measurement distance (FF) to the workpiece surface 190.

As illustrated, the optical pen 120 has a measuring range R that is bound by a minimum range distance ZMIN and a maximum range distance ZMAX, and the surface 190 to be measured should fall within the measuring range R. The general measuring range R of an optical pen 120 may be in the range of tens of microns to a few millimeters, which may be adjustably set based on configuration of the axial chromatic aberration portion 150. The measuring range R in some instances of known optical pens may be approximately 1/10 to 1/2 of the nominal working distance from the end of the pen. As used herein, the nominal working distance (S) of the optical pen 120 is defined as a distance from a distal end of the optical pen 120 (including an optical reflective element 155, to be described in detail below) to the surface 190 to be measured, as shown in FIG. 1.

In various embodiments, it may be advantageous if the maximum and minimum range distances of the measuring ranges (i.e., ZMAX and ZMIN of the measuring range R) are determined according to certain optical system constraints. Briefly, a first factor in determining the minimum and maximum of the measuring ranges is the physical distance, which the specified set of lenses in the axial chromatic aberration portion 150 is able to focus a specified set of wavelengths over, with a specified level of accuracy. More generally, each range with its minimum and maximum limits generally corresponds to the range, which the available input spectrum can be well focused over, by using chromatic aberration. In addition, the limitations of the wavelength detector itself (see 162 in FIG. 1) are another factor in the ranges. In other words, for the different anticipated and desired wavelengths that are to be measured, it is desirable that the wavelengths be spread across the array of the detector 162 so that a high level of resolution may be achieved. In summary, the ranges with the specified minimum and maximum distances are generally determined by limitations related to the ability to focus the spectrum effectively over a distance along the specified axis and by design choices related to the dispersion of the wavelengths on the detector 162.

The electronics portion 160 includes a fiber coupler 161, the wavelength detector 162, the light source (source light generating portion) 164, a signal processor 166 and a memory portion 168. In various embodiments, the wavelength detector 162 includes a spectrometer or spectrograph arrangement wherein a dispersive element (e.g., a grating) receives the reflected measurement light through the optical fiber cable 112 and transmits the resulting spectral intensity profile to a detector array 163. The wavelength detector 162 may also include related signal processing (e.g., provided by the signal processor 166 in some embodiments) that removes or compensates certain detector-related error components from the spectral intensity profile. Thus, certain aspects of the wavelength detector 162 and the signal processor 166 may be merged and/or indistinguishable in some embodiments.

Figure 2:
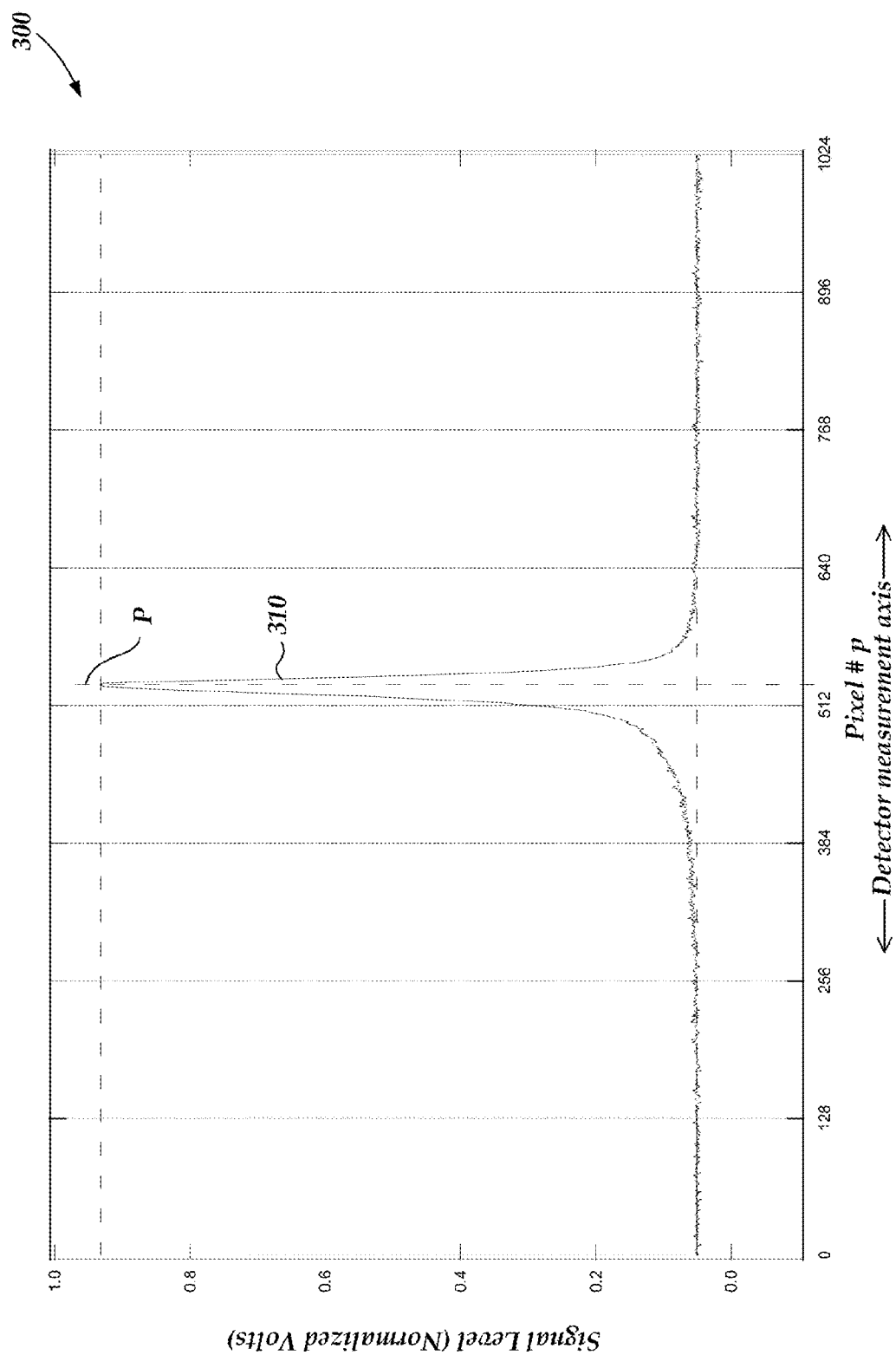
FIG. 2 is a diagram of a spectral intensity profile obtainable by a CPS, including a spectral peak component that may correspond to a unique distance from the optical pen to the interior surface along a corresponding unique measurement direction.

The white light source 164, which is controlled by the signal processor 166, is coupled through the optical coupler 161 (e.g., a 2×1 optical coupler) to the fiber cable 112. As described above, the measurement light based on the source light travels through the optical pen 120, which produces longitudinal chromatic aberration so that its focal length changes with the wavelength of the light. The wavelength of measurement light that is most efficiently transmitted back through the fiber is the wavelength that is in focus on the surface 190 at the position Z. The reflected wavelength-dependent measurement light intensity then passes through the fiber coupler 161 again to be directed to the wavelength detector 162, which generates a spectral intensity profile. The detector array 163 receives the spectral intensity profile, which is distributed over an array of pixels along a measurement axis of the detector array 163. FIG. 2 is a sample diagram of a spectral intensity profile 310 from the detector array 163, including a spectral peak component that corresponds to a unique distance from the optical pen 120 to the interior surface of a hole to be measured, according to the principles disclosed herein. Briefly, a subpixel-resolution distance indicating the coordinate of the spectral peak component "P" in FIG. 2 is calculated by the signal processor 166, and the distance indicating the coordinate determines the measurement distance (FF) to the surface 190 (at Z) via a distance calibration lookup table stored in the memory portion 168. For example, in FIG. 2, a subpixel-resolution distance of about 620.6 pixels indicative of the wavelength peak component "P" is determined, and the subpixel-resolution distance is converted to the measurement distance (FF) in microns or millimeters. The subpixel-resolution distance indicative of the peak coordinate may be determined by various methods such as determining the centroid in a spectral peak component of the spectral intensity profile.

Figure 3:
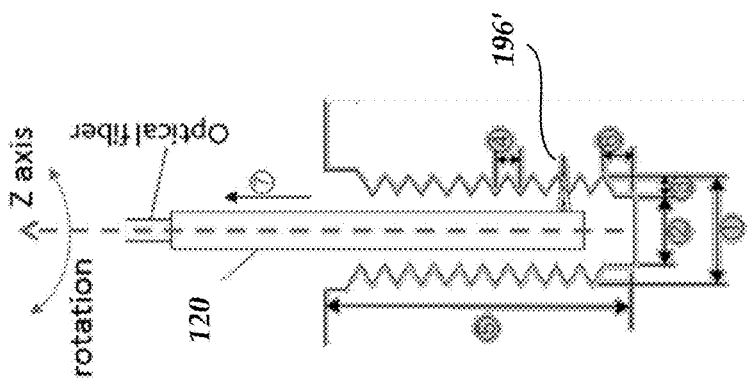

In FIG. 1, the optical pen 120 may optionally include a reflective element 155 shown in dashed outline. The reflective element 155 may be placed in the path of the measurement light ML outputted from the axial chromatic aberration portion 150 to redirect the measurement light 196' along the measurement direction MD' that is generally perpendicular to the original measurement direction of MD. The measuring range R' along the redirected measurement direction MD' is the same as the measuring range R along the original measurement direction MD and is also bound by XMIN and XMAX. In such an implementation, the reflective element 155 directs the measurement light 196' along the measurement direction MD' that is different from (e.g., orthogonal to) the optical axis OA as needed in some measurement applications. For example, such orthogonal orientation as illustrated is currently utilized to measure a geometric characteristic of a hole, such as a hole diameter as shown in FIG. 3. FIG. 3 shows that an optical pen 120 having its measurement light 196' propagate in the orthogonal measurement direction MD', as shown in FIG. 1, may be rotated about its central Z axis to measure an outer diameter of a threaded hole ①, an inner diameter of the threaded hole ②, and a thread height (or a depth of the threads) ③, which is the difference between ① and ②.

Figure 4:
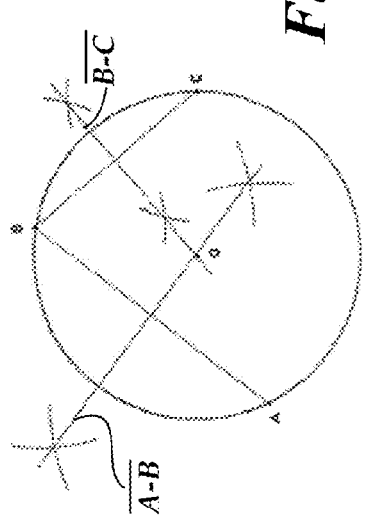
FIG. 4 illustrates the general concept of measuring a characteristic of a hole, such as a diameter of the hole having a circular cross-section, based on at least three measurement points taken on the interior surface of the hole.

Specifically, as shown in FIG. 4, measurement of a geometric characteristic of a hole, such as a diameter of a circle, requires determination of at least three points on the interior surface of a hole. FIG. 4 illustrates that three sets of X and Y coordinates (i.e., three points A, B and C) are required at a minimum in order to determine the diameter of the circle, or the diameter of a hole at a given Z height as shown in FIG. 3. In FIG. 4, once the locations of three points A, B and C are determined, an equidistant line $\overline{A\text{-}B}$ is drawn between points A and B, and another equidistant line $\overline{B\text{-}C}$ is drawn between points B and C. The center O of the circle can then be determined as the intersection between the equidistant lines $\overline{A\text{-}B}$ and $\overline{B\text{-}C}$. The distance from O to any of the three points (A, B or C) is the radius of the circle, and the diameter of the circle is obtained as twice the radius. As shown in FIG. 3, obtaining at least three measurement points on the interior surface of a hole, such as a circle, currently requires rotating an optical pen 120 such that its measurement direction MD' intersects the interior surface of a hole at three different positions. As discussed in the background section above, however, having to rotate an optical pen 120 requires complex opto-mechanical parts to effect the rotation, is time-consuming and thus lowers measurement throughput, and inevitably introduces some level of runout and/or wobble and related measurement errors.

Figure 5:
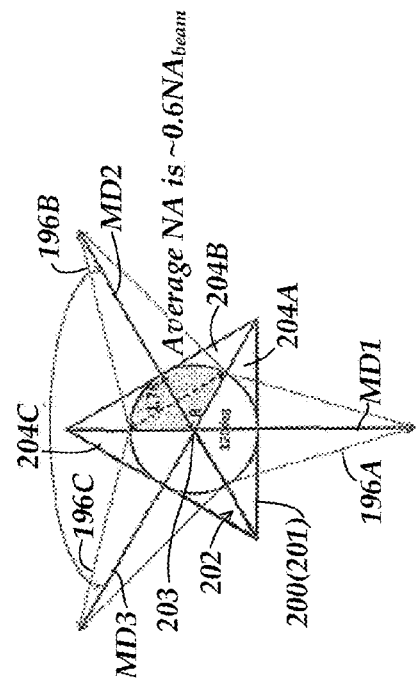
FIG. 5 illustrates an example of a beam dividing deflecting element in the form of a right triangular pyramid shaped reflective optical element, which includes three planar reflective facets, according to some embodiments of the present invention.
Figure 7:
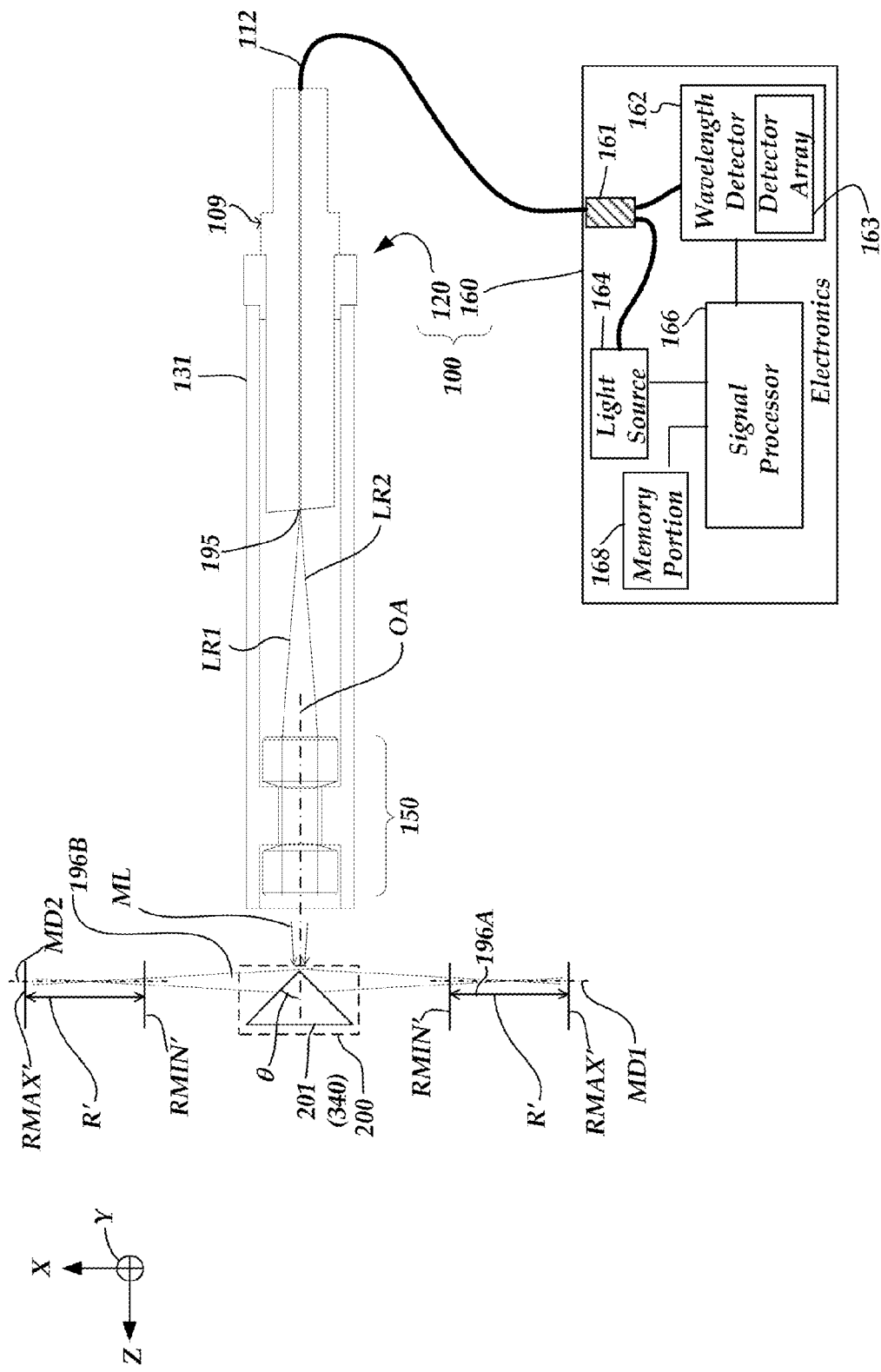
FIG. 7 is a block diagram of an exemplary CPS including an optical pen that outputs measurement light, wherein the optical pen includes a beam dividing deflecting element arranged to distribute the measurement light simultaneously along at least three measurement directions according to embodiments of the present invention.

In various applications, it may be desirable to be able to measure at least three points of the interior surface of a hole without having to rotate the optical pen 120. In accordance with one embodiment, as shown in FIGS. 5 and 7, a beam dividing deflecting element 200 in the form of a pyramid shaped reflective optical element 201 is provided, which can be attached to the distal end of an optical pen 120 (in lieu of the reflective element 155 of FIG. 1). The beam dividing deflecting element 200 permits measurement of a geometric characteristic of a hole, such as a circle diameter, without having to rotate the optical pen 120.

As shown in FIG. 5, the right triangular pyramid shaped reflective optical element 201 has a triangular base 202, has an apex 203 aligned directly above the center of the triangular base 202, and includes a first, second, and third planar reflective facets 204A, 204B and 204C corresponding to at least three measurement directions MD1, MD2 and MD3, respectively. For example, the pyramid shaped reflective optical element 201 may be a right triangular pyramid prism with mirror coating applied to each of the planar reflective facets 204A, 204B and 204C. Referring additionally to FIG. 7, the pyramid shaped reflective optical element 201 is arranged such that its apex 203 faces the incoming measurement light ML. The three planar reflective facets 204A, 204B and 204C receive the measurement light ML and distributes (reflects) the measurement light 196A, 196B and 196C simultaneously along at least three measurement directions MD1, MD2 and MD3, respectively, which are transverse to the central Z axis, toward the interior surface of a hole to be measured. A hole may have a circular cross-section, a non-circular cross-section (e.g., square cross-section), and may be only partially surrounded by an interior surface of a circular or non-circular cross-section.

Figure 6:
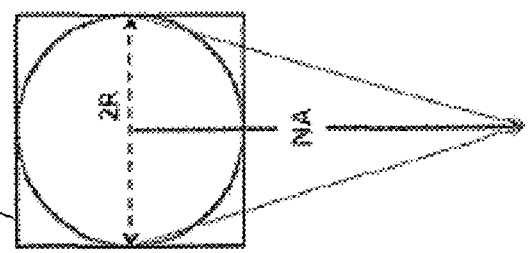
FIG. 6 illustrates a radius and a numerical aperture (NA) of a conventional reflective element that may be coupled to a distal end of an optical pen and rotated to measure characteristics of a hole.

In various exemplary embodiments, the at least three measurement directions MD1, MD2 and MD3 are distributed evenly around 360 degrees. For example, in the illustrated embodiment of FIG. 5, each adjacent pair of the three measurement directions MD1, MD2 and MD3 forms an angle of 120 degrees, with each of the planar reflective facets 204A, 204B and 204C having an effective numerical aperture (NA) of about 0.6 NA as compared to the NA of the incident measurement light ML. Specifically, the numerical aperture of about 0.6 NA is based on the average beam diameter of 1.2 R, which is bisected by each of the measurement directions MD1, MD2 and MD 3 as shown in FIG. 5, wherein R is the radius of the incident beam ML projected onto the triangular base 202 of the pyramid shaped reflective optical element 201. On the other hand, as shown in FIG. 6, the numerical aperture of the reflective element 155 of FIG. 1 is NA, which is the same as the NA of the measurement light ML incident on the reflective element 155. NA is based on the beam triangle base of length 2 R that is bisected by the measurement direction MD, where R is the radius of the reflective element 155. It should be noted that the numerical aperture of about 0.6 NA associated with the pyramid shaped reflective optical element of 201 is not significantly smaller than the numerical aperture NA of the reflective element 155 of FIG. 1, and is suited for receiving and outputting sufficient amount of measurement light for the purpose of performing a chromatic confocal point sensing measurement according to various embodiments of the present invention.

FIG. 7 schematically shows two of the three measurement light beams 196A, 196B reflected from two of the planar reflective facets, though in reality three measurement light beams are reflected from three planar reflective facets, respectively. Specifically, in FIG. 7, the first measurement light 196A reflected from the first planar reflective facet 204A propagates along the first measurement direction MD1, and the second measurement light 196B reflected from the second planar reflective facet 204B propagates along the second measurement direction MD2. The optical pen 120 has the same measuring range R', bound by RMIN' and RMAX', along each of the first and second measurement directions MD1 and MD2, as illustrated. Though not shown in FIG. 7, the third measurement light 196C reflected from the third planar reflective facet 204C propagates along the third measurement direction MD3 and has the same measuring range R' also bound by RMIN' and RMAX'.

Figure 8:
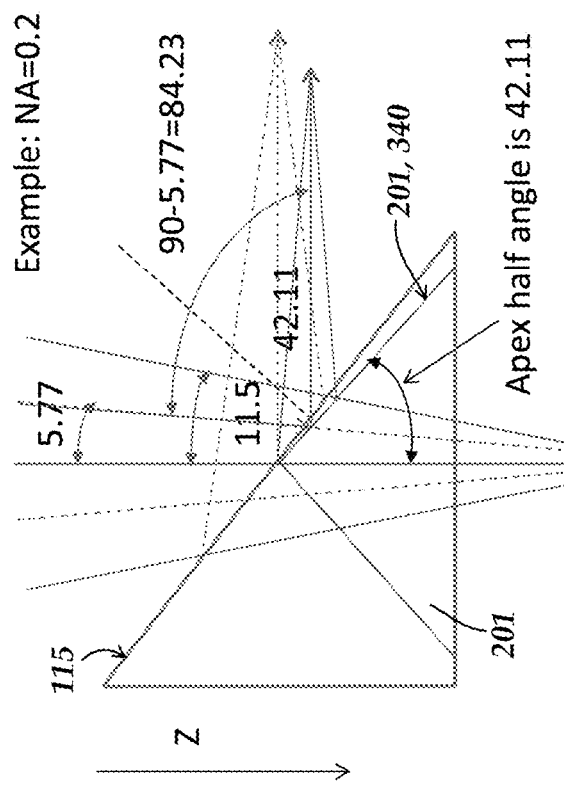
FIG. 8 illustrates general consideration in configuring a beam dividing deflecting element, in the form of a right triangular pyramid shaped reflective optical element including at least three planar facets, or a cone-shaped reflective optical element, to be included in an optical pen according to exemplary embodiments of the present invention.

FIG. 8 illustrates general consideration in configuring the beam dividing deflecting element 200 in the form of the pyramid shaped reflective optical element 201. FIG. 8 also applies to the embodiment in which the beam dividing deflecting element 200 is formed of a cone-shaped optical element 340 to be described below in reference to FIGS. 15-17. Generally, apex half angle of the pyramid shaped reflective optical element 201 (or the cone-shaped optical element 340) may be calculated as:

$$\text{Apex half angle}=45-\{\sin^{-1}(NA)\}/4 \qquad \text{Eq. (1)}$$

For example, assuming that the numerical aperture NA of the incident beam ML is 0.2 then the apex half angle is calculated to be 42.11 degrees.

FIG. 8 shows the cross-section of the pyramid shaped reflective optical element 201 (or the cone-shaped optical element 340), in comparison to the cross-section of the reflective element 115 as shown in FIG. 1. For the pyramid shaped reflective optical element 201 or the cone-shaped optical element 340, the half angle of the reflecting surface apex with respect to the central Z axis and within the plane of the central Z axis and the measurement light is preferably less than 45 degrees in order for the chief ray of the measurement light to be at 90 degrees with respect to the central Z axis of the optical pen. The 42.11 degrees of apex half angle calculated above satisfies this requirement. In various exemplary embodiments, the general rule is that the half angle of the apex should be less than 45 degrees by ¼ of the NA angle of the measurement light ML, as shown in FIG. 8.

According to various embodiments, the method is capable of measuring a geometric characteristic of a hole with a measurement resolution of at least as fine as 5 microns.

Figure 9A:
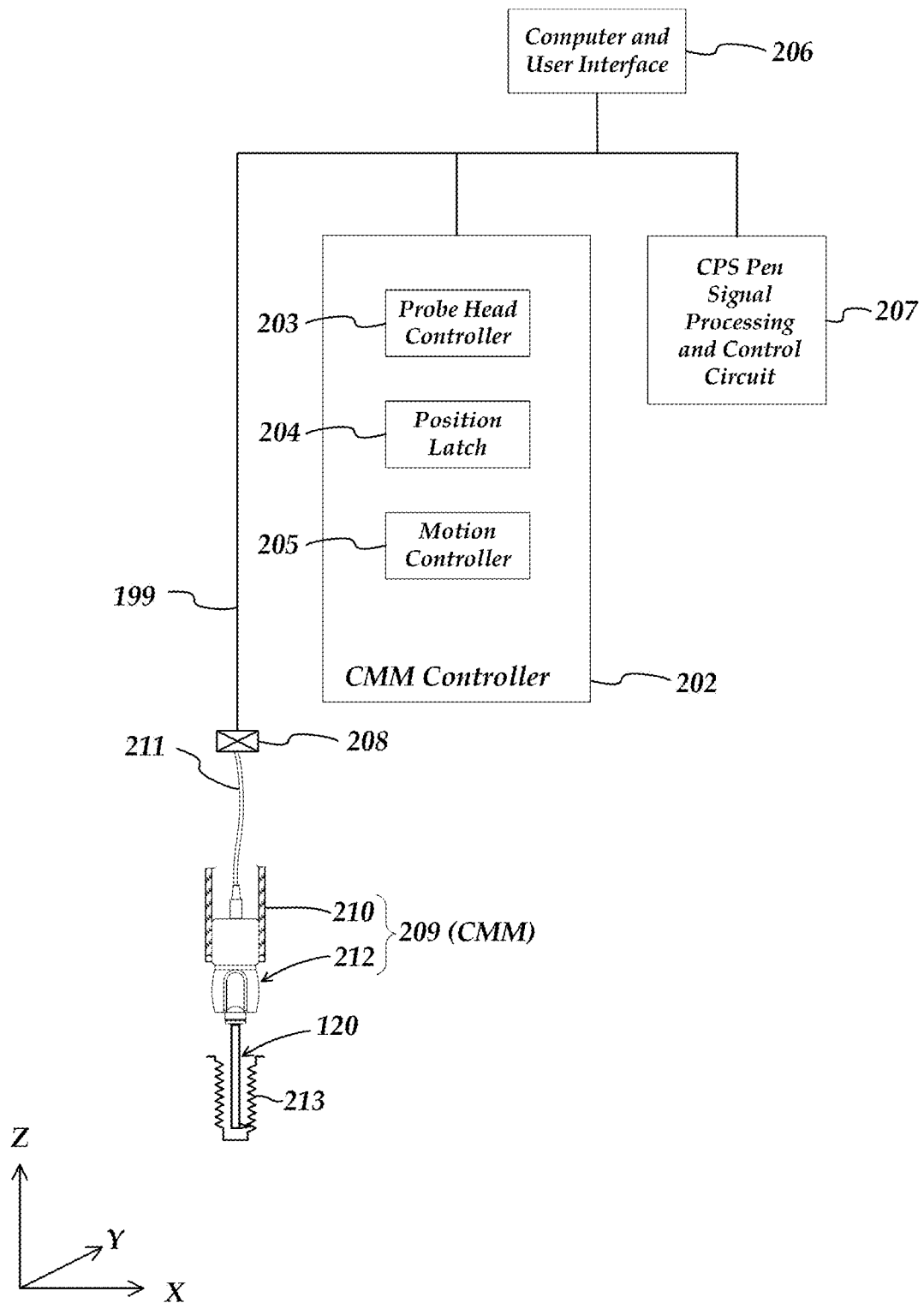
FIG. 9A is a block diagram of a chromatic confocal point sensor (CPS) system including an optical pen and an electronics portion, which may be coupled to an external device in the form of a coordinate measuring machine (CMM) including a CMM controller and a user interface, suitable for executing various methods of inspecting a geometric characteristic of a hole according to exemplary embodiments of the present invention.

In applications to inspect various geometric characteristics of holes, the optical pen 120 may be coupled to any coordinate measuring machine (CMM) known in the art, which is capable of controlling the precise position of the optical pen 120 along each of X, Y and Z axes. Typically, a CMM has a bridge movable along one axis of the XY plane, and a carriage movable along the bridge along the other axis of the XY plane. The Z-axis movement is provided by a vertical quill that moves up and down through the carriage. As shown in FIG. 9A, the distal end of the vertical quill 210 of a CMM 209 includes a probe head 212 configured to receive a variety of interchangeable elongated probes, such as the optical pen 120 according to various embodiments of the present invention. In one embodiment, the probe head 212 of the CMM may incorporate the standard Renishaw™ autojoint connection configuration most commonly used for certain applications in the industry, available from Renishaw Metrology Ltd. in Gloucestershire, UK. In the example of FIG. 9A, the optical pen 120 is coupled to the probe head 212 to inspect a geometric characteristic of a hole including screw threads 213. The CMM communicates with other components through a data transfer line 199 (e.g., a bus), which is connected by a connector 208 (e.g., a "micro-D" type connector) to a probe head cable 211 that provides signals to and receives signals from the optical pen 120. The CMM 209, to which the optical pen 120 is coupled, is controlled by a CMM controller 202, while the optical pen 120 exchanges data with, and is controlled by, the CPS pen signal processing and control circuit 207 (e.g., in one embodiment provided by the signal processor 166 and the memory portion 168 in the electronics portion 160 of FIG. 1). The user may control all of the components through the computer and user interface 206.

The CMM controller 202 includes a probe head controller 203 configured to control operation of the probe head 212, and a motion controller 205 specifically configured to control the precise position and movement of the probe head 212 and hence of the optical pen 120 in X-, Y- and Z-directions, as known in the art. The CMM controller 202 also includes a position latch 204 that produces an XYZ position of the probe head 212. A corresponding position latch included in the CPS pen signal processing and control circuit 207 produces an XYZ latch signal of the optical pen 120, and communicates with the position latch 204 in the CMM controller 202 to synchronize the coordinates of the CMM 209 with the measurement coordinates of the optical pen 120. Thus, geometric characteristics of a hole, such as the location of the center of the hole, which is inspected by the optical pen 120 coupled to the CMM may be determined based on CMM coordinates that correspond to the position of the optical pen 120 placed inside the hole.

As will be more fully described below, according to various embodiments of the present invention, methods are provided that allow a user to inspect or measure a geometric characteristic of a hole of a workpiece with a CPS pen without having to rotate the pen. In various applications, the methods involve positioning the optical pen 120 in a hole to determine at least three measurement points of the interior surface of the hole, without having to rotate the optical pen 120. In further applications, the methods involve linearly moving the optical pen 120 along one or more of the X, Y and Z axes, to thereby determine at least three measurement points of the interior surface of the hole, without having to rotate the optical pen 120. Such linear translations of the optical pen 120 can be readily accomplished by any standard CMM, to which the optical pen 120 may be coupled. The instructions to inspect a workpiece including various features to be inspected, such as holes, are typically embodied in a workpiece program or a part program that can be executed by the CMM.

As another example, the optical pen 120 may be used in connection with a machine vision inspection system known in the art, such as QUICK VISION® QV Apex series of microscopic-type vision systems available from Mitutoyo America Corporation in Aurora, Ill. Briefly, a machine vision inspection system includes a movable vision (camera) system and a movable stage, on which a workpiece to be visually inspected is placed. The vision system and/or the stage are movable along X-, Y- and Z axes such that the vision system can acquire a complete image of the workpiece placed on the stage for inspection and analysis purposes. The instructions to acquire an image of a workpiece including various features to be inspected, such as holes, and to inspect the acquired image are typically embodied in a workpiece program or a part program that can be executed on the machine vision inspection system. Some of the vision systems may include a probe sub-system configured to hold a specialized probe, such as the optical pen 120 according to various embodiments of the present invention. Thus, by coupling the optical pen 120 to the probe sub-system of the vision system, a user can utilize the controller of the machine vision inspection system to control the position and linear movement of the optical pen 120 along X-, Y- and Z-directions, to thereby obtain at least three measurement points of the interior surface of a hole, similarly to using a CMM to control the position and linear movement of the optical pen 120. In this configuration, standard CMM techniques may be utilized in conjunction with standard machine vision techniques to control the probe sub-system to automatically position and move the optical pen 120 and hence the beam dividing deflecting element 200 of the optical pen 120 in relation to the hole to be measured according to various embodiments of the present invention.

Figure 9B:
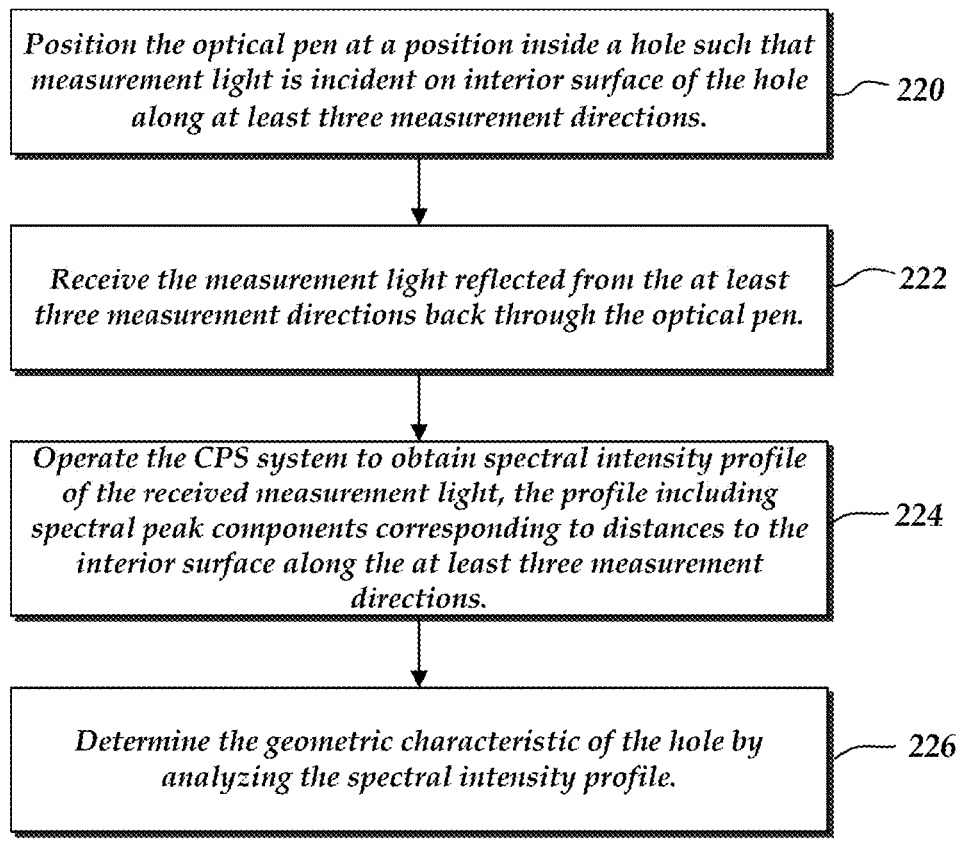
FIG. 9B is a flowchart of a method for using a CPS system to inspect a geometric characteristic of a hole, according to exemplary embodiments of the present invention.

FIG. 9B is a general flowchart of a method for using a CPS system to inspect a geometric characteristic of a hole, according to exemplary embodiments of the present invention.

In block 220, the first step is a step of positioning the optical pen 120 at a position inside the hole such that the measurement light is incident on the interior surface along at least three measurement directions. For example, the electronics portion 160 of the CPS 100 operates such that the measurement light is incident on the interior surface along the at least three measurement directions.

In block 222, the second step is a step of receiving the measurement light reflected from the at least three measurement directions back through the confocal aperture 195 of the optical pen 120 placed at said position in the hole. For example, the spectrometer (in 162 of FIG. 7) receives the measurement light reflected from the at least three measurement directions back through the confocal aperture 195.

In block 224, the third step is a step of operating the CPS system to obtain a spectral intensity profile of the measurement light (see FIG. 2), wherein the spectral intensity profile includes spectral peak components corresponding to distances to the interior surface that are within the optical pen's measuring range "R" along the at least three measurement directions. The spectral peak components may or may not be isolated from each other, as will be described in various examples below.

In block 226, the fourth step is a step of determining the geometric characteristic of the hole based at least partially on signal processing operations comprising analyzing the spectral intensity profile to determine at least a first distance measurement from the optical pen 120 to the interior surface along at least a first measurement direction.

The fourth step of block 226 may be carried out by the electronics portion 160 of the CPS 100, by an external system such as a CMM to which the CPS 100 is coupled, or by a combination of both in various embodiments of the present invention. For example, the fourth step of block 226 may in turn include at least one of the following steps a), b) and c), below:

a) the signal processor of the electronics portion 160 determines the geometric characteristic of the hole based at least partially on signal processing operations comprising analyzing the spectral intensity profile to determine at least a first distance measurement from the optical pen to the interior surface along at least a first measurement direction;

b) the signal processor of the electronics portion 160 analyzes the spectral intensity profile to determine at least a first distance measurement from the optical pen to the interior surface along at least a first measurement direction, and outputs the at least first distance measurement to an external system, such as a CMM, configured to determine the geometric characteristic of the hole based at least partially on the at least first distance measurement; and c) the signal processor of the electronics portion 160 outputs the spectral intensity profile to an external system, such as a CMM, configured to determine the geometric characteristic of the hole based at least partially on signal processing operations comprising analyzing the spectral intensity profile to determine at least a first distance measurement from the optical pen to the interior surface along at least a first measurement direction.

In various embodiments, the hole to be measured has a radius r and the method of the invention may include configuring or selecting the optical pen 120 such that its measuring range R along each of the at least three measurement directions extends at least a distance RMAX' from its central Z axis, where RMAX'>r. This helps ensure that the interior surface of the hole to be inspected fits within the measuring range R of the optical pen 120 along all measurement directions. Then, the first step of positioning the optical pen 120 at a position inside a hole (block 220) may include positioning the optical pen 120 approximately centered in the hole such that all the spectral peak components in the spectral intensity profile substantially coincide to form a combined spectral peak indicative of an average radius of the interior surface along the at least three measurement directions. For example, the first step may include positioning the optical pen 120 at a position that provides the highest or narrowest combined spectral peak among those obtained by the optical pen 120 placed at a plurality of positions in the hole. This result is achievable with the pyramid shaped reflective optical element 201 described above or with the cone-shaped reflective optical element to be described below in reference to FIGS. 15-17. When the optical pen 120 is coupled to a CMM, the CMM can be used to position the optical pen 120 at an approximate center of the hole. For example, a part program for inspecting a particular workpiece including workpiece features, such as holes to be inspected, defines the size and position of each of the holes on the workpiece and, thus, a CMM can position and orient the optical pen 120 relative to the hole in the CMM coordinate system in reference to the part program. The location of the center of the hole may be determined based on CMM coordinates that correspond to the position of the optical pen 120 as controlled by the CMM.

Because a CMM may position and orient the optical pen 120 relative to a hole to be inspected in the CMM coordinate system, in various exemplary embodiments of the present invention, the first step of positioning the optical pen 120 at a position inside a hole (block 220) may include positioning the optical pen 120 off center in the hole such that at least three spectral peak components in the spectral intensity profile are obtained as isolated spectral peak components respectively corresponding to the distances from the optical pen 120 to the interior surface along the at least three measurement directions. For example, when the optical pen 120 is coupled to a CMM executing a part program, the location and orientation of the measuring range R of the optical pen 120 along each of the at least three measurement directions can be known and/or calibrated by the CMM. Thus, the CMM can precisely position and orient the optical pen 120 within the hole such that the at least three measurement directions extend toward at least three desired (predetermined) points on the interior surface of the hole while ensuring that these at least three points to be inspected respectively fall within the measuring range R of the light along the at least three measurement directions. Then, the measurement light reflected from the at least three measurement directions respectively form at least three spectral peak components that are isolated from each other in a single intensity profile. The at least three spectral peak components can be used to determine at least three distance measurements from the optical pen 120 to the interior surface along the at least three measurement directions, respectively.

In other embodiments and applications, not all three or more spectral peak components are isolated from each other in a single spectral intensity profile. For example, when a hole (or hole diameter) is too large relative to the optical pen's measuring range R, only one spectral peak component along one measurement direction can be determined in one spectral intensity profile. Specifically, when the hole has a circular cross-section having a radius r, the optical pen's measuring range R along each of the at least three measurement directions may extend at most a distance RMAX' from its center Z axis, wherein RMAX'<r. As another example, some applications may require determining one spectral peak component at a time in a single spectral intensity profile, such as when determining the location of one side of a square hole. In these embodiments and applications, the first step of positioning the optical pen 120 at a position inside a hole (block 220) may include positioning the optical pen 120 at a first off center position in the hole such that at least a first spectral peak component in the spectral intensity profile is an isolated spectral peak component corresponding to a unique distance from the optical pen 120 to the interior surface along a corresponding unique measurement direction at the first off center position. The angular direction of a point on the interior surface that has generated the first spectral peak component, relative to the optical pen 120, can be inferred from the direction of the first off center position from the nominal center of the hole 301, which is typically known based on the initial set up of the CPS system and/or a part program used to inspect the hole 301.

Then, when the optical pen 120 is coupled to a CMM and the CMM is used to position the optical pen 120 in the hole, the steps of positioning the optical pen 120 (block 220), receiving the measurement light (block 222) and operating the CPS system to obtain a spectral intensity profile (block 224) can be repeated corresponding to second and third off center positions of the optical pen 120, respectively. As a result, at least second and third isolated spectral peak components are obtained in second and third spectral intensity profiles, respectively, which are isolated spectral peak components corresponding to unique distances from the optical pen to the interior surface along corresponding unique measurement directions at the second and third off center positions, respectively. The step of determining the geometric characteristic of the hole (block 226) includes: (a) analyzing at least the first, second and third spectral intensity profiles to determine at least first, second and third distance measurements from the optical pen to the interior surface along the corresponding unique measurement directions at the first, second and third off center positions, and (b) determining the geometric characteristic of the hole based on at least the first, second and third distance measurements and CMM coordinates respectively corresponding to the first, second and third off center positions.

Figure 11:
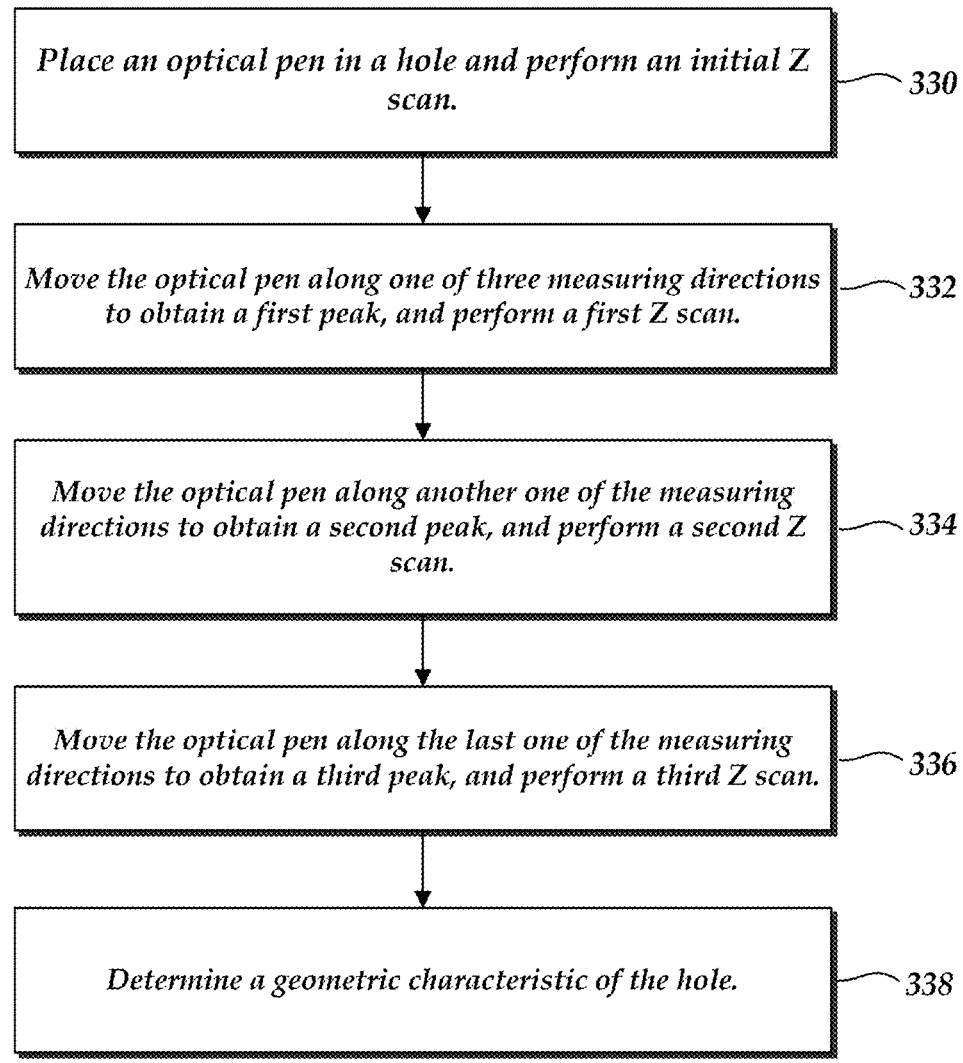
FIG. 11 is a flowchart of steps performed in the method illustrated in FIGS. 10A-10D.

FIGS. 10 and 11 illustrate a method of isolating one spectral peak component at a time, i.e., in a single spectral intensity profile, and repeating the process at least three times to obtain at least three isolated spectral peak components. Referring specifically to FIG. 10A, in this embodiment, it is assumed that a diameter D of a hole 301 is large relative to the optical pen's measuring range R' to satisfy the following relationship:

$$s+d/2+R'/2<D/2 \qquad \text{Eq. (2)}$$

wherein s is a working distance of the optical pen 120 that is situated inside the hole 301 (see FIG. 1), d is a diameter of the optical pen 120 which fittedly receives therein the beam dividing deflecting element 200, and R' is the measuring range of the optical pen.

Referring additionally to FIG. 11, which is a flowchart illustrating an exemplary method, in block 330, the optical pen 120 including the beam dividing deflecting element 200 is placed inside the hole 301. As described above in reference to FIG. 7, the optical pen 120 has a confocal aperture 195 and projects the measurement light beams 196A, 196B and 196C along at least three measurement directions MD1, MD2 and MD3, respectively. After the optical pen 120 is placed inside the hole 301, an initial Z scan is performed to obtain a series of coordinates (X0, Y0) of the center of the optical pen 120 along the Z axis by moving the optical pen 120 along the Z axis, which are collectively referred to as an initial Z scan. The initial Z scan is obtained to generate reference coordinates (X0, Y0) of the optical pen 120 for each value along the Z axis. During the initial Z scan, because the hole 301 is assumed to be large relative to the optical pen's measuring range, it is expected that the interior surface of the hole 301 is outside the measuring range R (or "RMAX"' of FIG. 7) of each of the measuring beams 196A, 196B and 196C. Thus, spectral data obtained at this time are expected to be weak so as not to include any distinct peak component.

At block 332 in FIG. 11, referring to FIG. 10B, the CMM is controlled to move the optical pen 120 along one of the three measurement directions. In the illustrated embodiment, the optical pen 120 is moved along the second measurement direction MD2, as indicated by an arrow 333, such that the interior surface of the hole 301, on which the second measurement light 196B impinges, comes within the measuring range R of the second measurement light 196B. Thus, the second measurement light 196B would produce a spectral peak component 321B, which may be used together with the initial Z scan data and the coordinates of the center of the optical pen 120 at this point (as shown in FIG. 10B) to obtain coordinates (X1, Y1) of the point at which the second measurement light 196B impinges on the interior surface of the hole 301. Then, the optical pen 120, which has been positioned relative to the hole 301 to obtain the first spectral peak component 321B, is moved along the Z axis in the hole 301 to obtain a series of coordinates (X1, Y1) as a function of Z. The Z scan at this point is referred to as a first Z scan, which is the first of three similar Z scans to be performed, as will be described below.

At block 334 in FIG. 11, referring to FIG. 10C, the CMM is controlled to move the optical pen 120 along another one of the three measurement directions. In the illustrated embodiment, the optical pen 120 is moved along the third measurement direction MD3, as indicated by an arrow 335, such that the interior surface of the hole 301, on which the third measurement light 196C impinges, comes within the measuring range R of the third measurement light 196C. Thus, the third measurement light 196C would produce a spectral peak component 321C, which may be used together with the initial Z scan data and the coordinates of the center of the optical pen 120 at this point (as shown in FIG. 10C) to obtain coordinates (X2, Y2) of the point at which the third measurement light 196C impinges on the interior surface of the hole 301. Then, the optical pen 120, which has been positioned relative to the hole 301 to obtain the second spectral peak component 321C, is moved along the Z axis in the hole 301 to obtain a series of coordinates (X2, Y2) as a function of Z. The Z scan at this point is referred to as a second Z scan, which is the second of three similar Z scans to be performed.

At block 336 in FIG. 11, referring to FIG. 10D, the CMM is controlled to move the optical pen 120 along the last one of the three measurement directions. In the illustrated embodiment, the optical pen 120 is moved along the first measurement direction MD1, as indicated by an arrow 337, such that the interior surface of the hole 301, on which the first measurement light 196A impinges, comes within the measuring range R of the first measurement light 196A. Thus, the first measurement light 196A would produce a spectral peak component 321C, which may be used together with the initial Z scan data and the coordinates of the center of the optical pen 120 at this point (as shown in FIG. 10D) to obtain coordinates (X3, Y3) of the point at which the first measurement light 196A impinges on the interior surface of the hole 301. Then, the optical pen 120, which has been positioned relative to the hole 301 to obtain the first spectral peak component 321A, is moved along the Z axis in the hole 301 to obtain a series of coordinates (X3, Y3) as a function of Z. The Z scan at this point is referred to as a third Z scan, which is the last one of three similar Z scans to be performed.

The first, second and third Z scans may be performed in the same direction along the Z axis in some embodiments, while in other embodiments one of these scans may be performed in the opposite direction along the Z axis, depending on each application and operation.

At this point, three sets of coordinates have been obtained: a series of coordinates (X1, Y1) indicative of a first position at which the second measurement light 196B impinges on the interior surface of the hole 301 as a function of Z; a series of coordinates (X2, Y2) indicative of a second position at which the third measurement light 196C impinges on the interior surface of the hole 301 as a function of Z; and a series of coordinates (X3, Y3) indicative of a third position at which the first measurement light 196A impinges on the interior surface of the hole 301 as a function of Z. Then, at block 338 of FIG. 11, a geometric characteristic of the hole 301, such as the hole diameter and the like, may be determined based on these three sets of coordinates indicative of three positions on an X-Y plane as a function of Z (i.e., along the Z axis).

In various applications, different optical pens 120 having different physical configurations (e.g., diameter) and optical characteristics (e.g., different measuring ranges R) may be provided, and an appropriate pen may be selected depending on the relative size of a hole to be measured.

In some exemplary applications of the invention, the interior surface of the hole includes screw threads, and the optical pen 120 is coupled to a CMM which is used to position the optical pen 120. The step of positioning the optical pen 120 at a position in the hole (block 220 in FIG. 9B) includes positioning the optical pen 120 at a current position, which corresponds to an axial position along a direction parallel to a central axis of the hole (i.e., Z direction) and a current off center position transverse to the central axis of the hole, such that at least a first spectral peak component in the corresponding spectral intensity profile is obtained as an isolated spectral peak component corresponding to a unique distance from the optical pen 120 to the interior surface along a corresponding unique measurement direction at the current position. The method further includes repeating the steps of positioning the optical pen 120 (block 220 in FIG. 9B), receiving the measurement light (block 222 in FIG. 9B), and operating the CPS system to obtain a spectral intensity profile (block 224 in FIG. 9B) at a plurality of different current positions that correspond to a plurality of different axial positions (along Z direction). A geometric characteristic of the hole including the screw threads, such as the tread height and the like, is determined by: (a) analyzing a plurality of spectral intensity profiles, respectively corresponding to the plurality of different current positions corresponding to the plurality of different axial positions, to determine a plurality of distance measurements from the optical pen 120 to the screw threads along a corresponding unique measurement direction at the plurality of different current positions that correspond to the plurality of different axial positions, and (b) determining the geometric characteristic of the screw threads based on at least some of the plurality of distance measurements at the plurality of different current positions that correspond to the plurality of different axial positions. CMM coordinates may be used to characterize at least some of the plurality of different current positions.

Figure 12A:
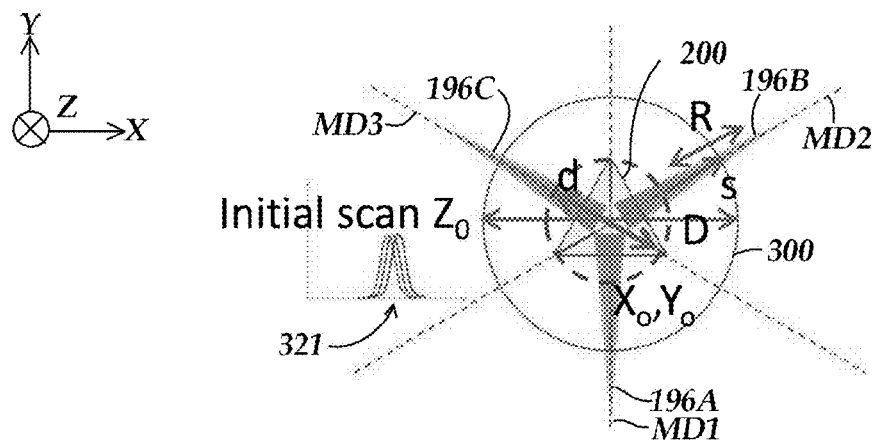
FIGS. 12A-12C schematically illustrate another method of operating a CPS optical pen to inspect a geometric characteristic of a hole, without having to rotate the optical pen, according to some embodiments of the present invention.
Figure 12B:
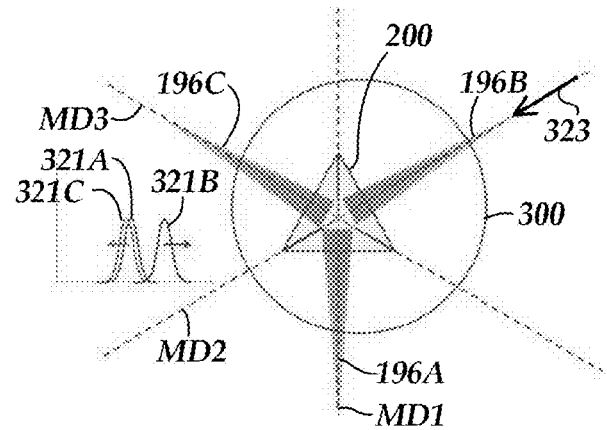
Figure 12C:
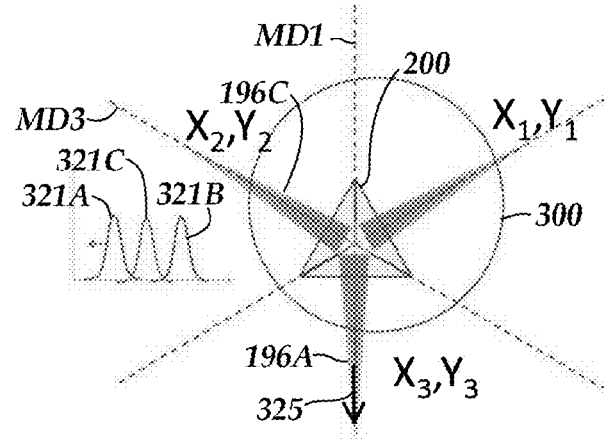
Figure 13:
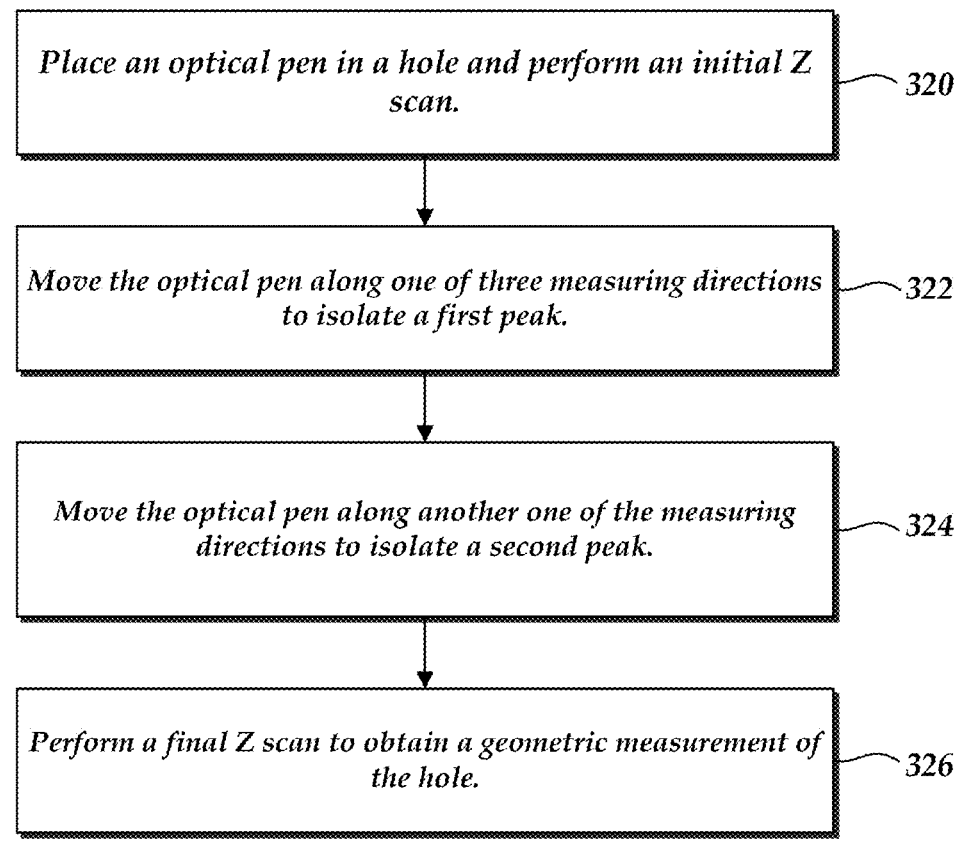
FIG. 13 is a flowchart of steps performed in the method illustrated in FIGS. 12A-12C.

FIGS. 12 and 13 describe another method of operating a CPS system to inspect a geometric characteristic of a hole, wherein the hole is rather small relative to the measuring range R of the optical pen 120, unlike the case described above in reference to FIGS. 10 and 11 where the hole is relatively large. Referring specifically to FIG. 12A, in this embodiment, it is assumed that a hole 300 has a diameter D that is small relative to the optical pen's measuring range R' to satisfy the following relationship:

$$s+d/2+R'/2>D/2 \qquad \text{Eq. (3)}$$

wherein s is a working distance of the optical pen 120 that is situated inside the hole 300 (see FIG. 1), d is a diameter of the optical pen 120 which fittedly receives therein the beam dividing deflecting element 200, and R' is a measuring range of the optical pen 120.

Referring additionally to FIG. 13, which is a flowchart illustrating an exemplary method, in block 320, the optical pen 120 including the beam dividing deflecting element 200 is placed inside the hole 300. As described above in reference to FIG. 7, the optical pen 120 has a confocal aperture 195 and projects at least three measurement light beams 196A, 196B and 196C along at least three measurement directions MD1, MD2 and MD3, respectively. When the optical pen 120 is placed inside the hole 300, coordinates (X0, Y0) of the center of the optical pen 120 are obtained by a CMM to which the optical pen 120 may be coupled. The optical pen 120 is scanned (moved) in Z direction so as to obtain a series of (X0, Y0) coordinates along the Z axis (initial Z scan). The initial Z scan is obtained to generate reference coordinates (X0, Y0) of the optical pen 120 for each value along the Z axis. During the initial Z scan, the three measurement light beams 196A, 196B and 196C are expected to travel approximately the same or similar distances to the interior surface of the hole 300 to thereby produce three spectral peak components 321 that generally coincide with each other. In this connection, the electronics portion 160 of the CPS 100 (and/or the CPS pen signal processing and control circuit 207 in FIG. 9A) is configured to process spectral data that contain three distinct peak components, i.e., to perform the spectral peak component generation processing as illustrated in FIG. 2 for each of the three distinct peak components.

At block 322 in FIG. 13, referring to FIG. 12B, the CMM is controlled to move the optical pen 120 along one of the three measurement directions. In the illustrated embodiment, the optical pen 120 is moved along the second measurement direction MD2, as indicated by an arrow 323, such that the distance that the second measurement light 196B travels to the interior surface of the hole 300 becomes longer than the distance that the other two measurement light beams (196A and 196C) travel to the interior surface of the hole 300. This will result in a spectral peak component 321B based on the second measurement light 196B shifting to longer wavelengths relative to the spectral peak components 321A and 321C based on the first and third measurement light beams 196A and 196C, respectively, which shift to shorter wavelengths. In effect, the spectral peak component 321B can be isolated from the rest of the spectral peak components 321A and 321C, as shown in FIG. 12B.

At block 324 in FIG. 13, referring to FIG. 12C, the CMM is controlled to move the optical pen 120 along another of the three measurement directions, such as the first measurement direction MD1, as indicated by an arrow 325. Thus, the distance that the first measurement light 196A travels to the interior surface of the hole 300 becomes shorter than the distance that the third measurement light 196C travels to the interior surface of the hole 300. This will result in a spectral peak component 321A based on the first measurement light 196A shifting to shorter wavelengths relative to the spectral peak component 321C based on the third measurement light 196C that shifts to longer wavelengths. In effect, the spectral peak component 321A can be isolated from the spectral peak component 321C, both of which have been isolated from the spectral peak component 321B based on the second measurement light 196B in FIG. 12B above. Thus, at this point, each of the three spectral peak component 321A, 321B and 321C is isolated from each other, when the optical pen 120 is positioned relative to the hole 300 in the manner illustrated in FIG. 12C.

At block 326 in FIG. 13, the optical pen 120, which has been situated so as to have the three spectral peak component 321A, 321B and 321C distinctively isolated from each other, is moved along the Z axis in the hole 300, to thereby obtain geometric measurements (e.g., diameters) of the hole 300 as a function of Z. The Z scan at this point is referred to as a final Z scan, in comparison to the initial Z scan performed in step 320 above (see FIG. 12A) to obtain a series of reference coordinates (X0, Y0). In some embodiments, both the initial Z scan and the final Z scan are performed in the same direction, while in other embodiments, the two scans may be performed in opposite directions along the Z axis. Various geometric characteristics of a hole, such as diameters and thread profile measurements (e.g., thread heights), may be determined based on the initial Z scan, i.e., the collection of (X0, Y0) reference coordinates along the Z axis, the coordinates of the center of the optical pen 120 after the optical pen 120 has been moved in the hole 300 to achieve three distinct spectral peak component, and the readings of the three distinct spectral peak component 321A, 321B and 321C. For example, for each value of Z along the Z axis, three measurement points on the X-Y plane where the three measurement light beams 196A, 196B and 196C intersect the hole 300 are obtained based on: (i) the initial Z scan, (ii) the coordinates of the center of the optical pen 120 after it has been moved to acquire three distinct spectral peak components, and (iii) the readings of the three distinct spectral peak component 321A, 321B and 321C. Then, based on the obtained three measurement points, the diameter D of the hole 300 (having a circular cross-section in the illustrated example) can be obtained using the principle illustrated in FIG. 4. As other examples, thread heights may be obtained (see ③ in FIG. 3) by calculating a difference between a distance to the bottom of a thread and a distance to the top of the thread.

It should be noted that the beam dividing deflecting element 200 may be provided by an optical element that is configured to receive and split the measurement light ML into four or more measurement light beams, such as a right pyramid with a square base including four planar reflective facets corresponding to four measurement directions that are separated by 90 degrees. However, additional measurement light beams are not necessary for the purpose of measuring a geometric characteristic of a hole, and further reduce the NA of each of the measurement light beams, which in turn requires extending the exposure/sample period to lower measurement throughput. Also, such configuration would be more difficult to fabricate and incorporate into the optical pen 120 than the pyramid shaped reflective optical element 201 described above. Thus, in accordance with various exemplary embodiments of the present invention, the beam dividing deflecting element 200 is a pyramid shaped reflective optical element having at most four planar reflective facets corresponding to at most four measurement directions.

Referring to FIG. 14 and again referring to FIG. 12A, another specific method is described of operating a CPS system to determine a radius or a diameter of a hole having a circular cross-section. As shown in FIG. 12A, in this embodiment, it is assumed that a hole 300 has a diameter D that is small relative to the optical pen's measuring range R to satisfy Equation (3) above such that the optical pen 120 that is positioned approximately at the center of the hole 300 will have the interior surface of the hole 300 within the measuring range R of each of the measurement light beams 196A, 196B and 196C.

Figure 14:
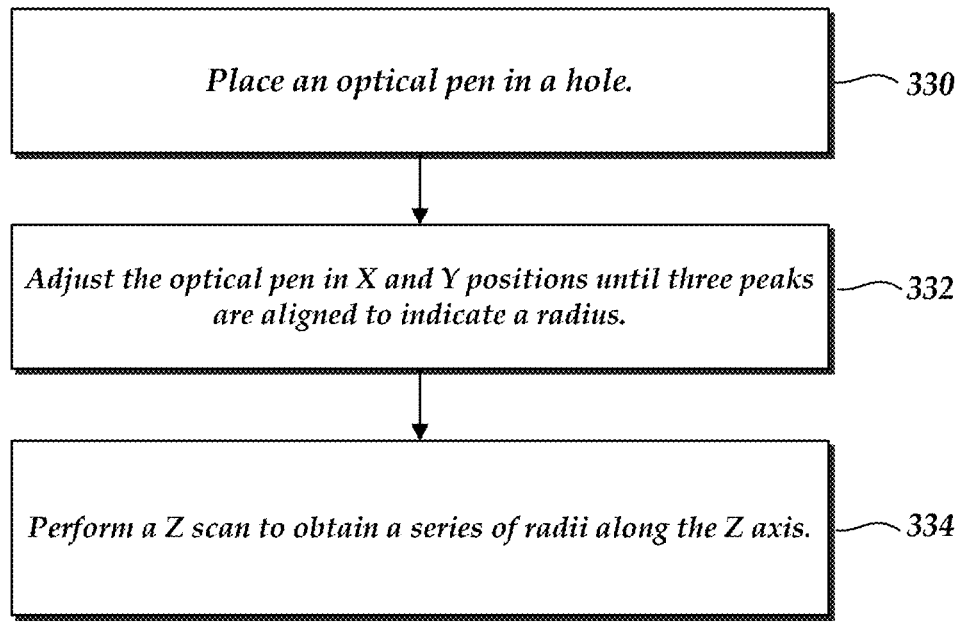
FIG. 14 is a flowchart of steps performed in yet another method of operating a CPS optical pen to inspect a radius of a hole having a circular cross-section, without having to rotate the optical pen, according to some embodiments of the present invention.

At block 330 of FIG. 14, the optical pen 120 is placed in the hole 300 approximately at the center of the hole. At this time, with the interior surface falling within the measuring range R of each of the measurement light beams, it is expected that three spectral peak components 321 based on the three measurement light beams 196A, 196B and 196C would generally coincide with each other, as shown in FIG. 12A.

At block 332 of FIG. 14, the CMM is controlled to adjust the position of the optical pen 120 on the X-Y plane until the center of the optical pen 120 substantially coincides with the center of the hole 301, at which point the three spectral peak components 321A, 321B and 321C will nominally precisely align with each other to produce a single high and/or narrow peak. Production of a single high and/or narrow peak indicates that the distance that each of the first, second and third measurement light beams 196A, 196B and 196C travels before impinging on the interior surface of the hole 300 is substantially identical, and thus, the distance can be considered as the radius of the hole 300. Therefore, the narrowly overlapping spectral peak components 321A, 321B and 321C at this point may be used as indicative of the radius of the hole 300. The height and/or narrowness of the overlapping spectral peak components to be indicative of a radius may be adjusted depending on each application.

At block 334 of FIG. 14, the optical pen 120, whose X-Y position has been adjusted such that a single high and/or narrow peak produced by the three measurement light beams 196A, 196B and 196C indicates the radius of the hole 300, may be moved along the Z axis in the hole 300 to obtain a series of radii as a function of Z.

Figure 17:
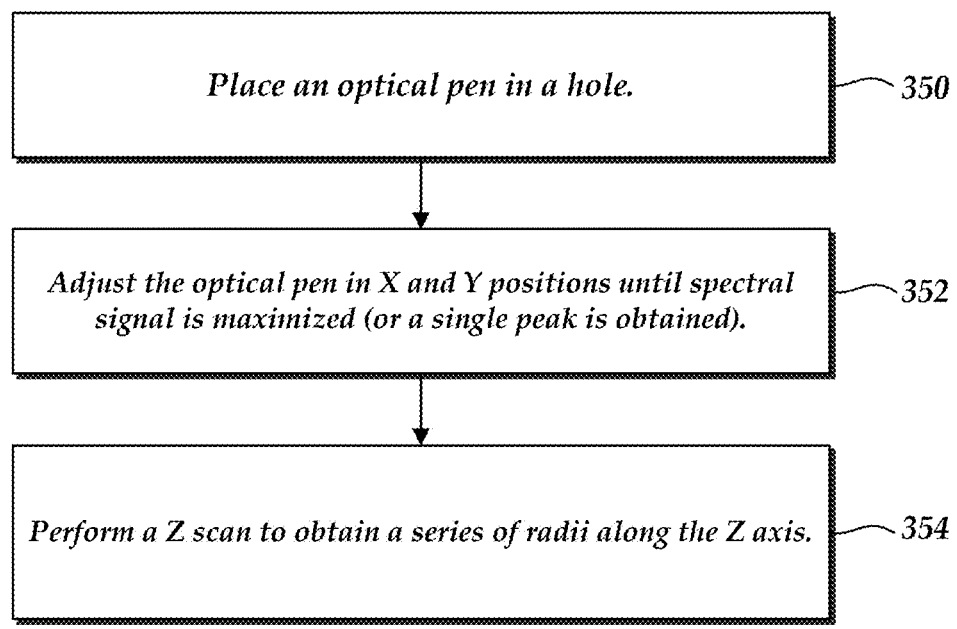
FIG. 17 is a flowchart of steps performed in the method illustrated in FIGS. 16A and 16B.

Next referring to FIGS. 15-17, a still further method is described of operating a CPS system for measuring a geometric characteristic of a hole, specifically, a radius or a diameter of a hole according to a further embodiment of the present invention. As shown in FIGS. 15A and 15B, the present embodiment utilizes a beam dividing deflecting element 200 in the form of a cone-shaped optical element 340. As shown in FIG. 7, the pyramid shaped reflective optical element 201 of the previously described embodiments may be replaced with the cone-shaped optical element 340 and the cone-shaped optical element 340 may be attached to the distal end portion of the optical pen 120, with its apex 340A facing the measurement light ML outputted from the confocal aperture 195 of the optical pen 120. As schematically illustrated in FIG. 15B, the cone-shaped optical element 340, upon receiving the measurement light ML, reflects the measurement light ML to produce a conical disk of measurement light 342 that radially projects toward the interior surface of a hole to be measured. The cone-shaped optical element 340 may be a cone-shaped prism with a mirror coating applied to its conical surface. In this connection, the electronics portion 160 of the chromatic confocal point sensor 100 (and/or the CPS pen signal processing and control circuit 207 in FIG. 9A) is configured to process spectral data that results from combining spectral signals based on multiple radial beams that together form the conical disk of measurement light 342.

At block 350 of FIG. 17, referring additionally to FIG. 16A, in this embodiment, it is assumed that a hole 300 having a diameter D is small relative to the optical pen 120 to satisfy Equation (3) above. Thus, the optical pen 120 that is positioned approximately at the center of the hole 300 will have the interior surface of the hole 300 within the measuring range R of the conical disk of measurement light 342. When the optical pen 120 is placed in the hole 300, unless the center of the optical pen 120 coincides with the center of the hole 300, it is expected that the spectral data will have a broad, weak peak based on multiple radial beams that together form the conical disk of measurement light 342.

At block 352 of FIG. 17, and referring to FIG. 16B, the CMM is controlled to adjust the position of the optical pen 120 on the X-Y plane until the center of the optical pen 120 substantially coincides with the center of the hole 300, at which point the multiple spectral peak components based on multiple radial beams that together form the conical disk of measurement light 342 nominally precisely overlap with each other to produce a more intense, narrow peak 360. Production of a single narrow peak 360 indicates that the distance that each of the multiple radial beams that collectively form the conical disk of measurement light 342 travels before impinging on the interior surface of the hole 300 is substantially identical, and thus, the distance can be considered as the radius of the hole 300. Therefore, the narrowly overlapping spectral peak component 360 at this point may be used as indicative of the radius of the hole 300. The narrowness of the overlapping spectral peak component to be indicative of a radius may be adjusted depending on each application.

At block 354 of FIG. 17, the optical pen 120, whose X-Y position has been adjusted such that the singularly overlapping narrow spectral peak component 360 based on the conical disk of measurement light 342 indicates the radius of the hole 300, may be moved along the Z axis in the hole 300 to obtain a series of radii as a function of Z.

Various embodiments of the systems and methods of the present invention have been described above. Various features of different embodiments may be selectively combined or replaced to create even further embodiments of the present invention. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for using a chromatic point sensor (CPS) system to inspect a geometric characteristic of a hole at least partially surrounded by an interior surface, the method comprising:
providing a CPS system including:
an electronics portion comprising a source light generating portion, a spectrometer, and a signal processor; and
an optical pen comprising a housing that extends along a central Z axis of the optical pen, a confocal aperture that outputs source light, an axial chromatic aberration portion arranged to input the source light and output measurement light that is focused with axial chromatic aberration, and a beam dividing deflecting element arranged to distribute the measurement light simultaneously along at least three measurement directions transverse to the central Z axis;
positioning the optical pen at a position inside the hole such that the measurement light is incident on the interior surface along the at least three measurement directions;
receiving the measurement light reflected from the at least three measurement directions back through the confocal aperture of the optical pen at the position;
operating the CPS system to obtain a spectral intensity profile of the measurement light, the spectral intensity profile comprising spectral peak components corresponding to distances to the interior surface that are within the optical pen's measuring range along the at least three measurement directions; and
determining the geometric characteristic based at least partially on signal processing operations comprising analyzing the spectral intensity profile to determine at least a first distance measurement from the optical pen to the interior surface along at least a first measurement direction.

2. The method of claim 1, wherein the hole has a circular cross-section.

3. The method of claim 2, wherein the hole has a radius r and the method comprises configuring or selecting the optical pen such that its measuring range along each of the at least three measurement directions extends at least a distance RMAX' from its central Z axis, wherein RMAX'>r.

4. The method of claim 3, wherein the step of positioning the optical pen at the position comprises positioning the optical pen approximately centered in the hole such that all the spectral peak components in the spectral intensity profile substantially coincide to form a combined spectral peak indicative of an average radius of the interior surface along the at least three measurement directions.

5. The method of claim 4, wherein the optical pen is coupled to a coordinate measuring machine (CMM), and the CMM is used to position the optical pen.

6. The method of claim 5, further comprising determining the location of the center of the hole based on CMM coordinates corresponding to the position.

7. The method of claim 4, wherein the step of positioning the optical pen at the position comprises positioning the optical pen at a position that provides the highest or narrowest combined spectral peak among those obtained at a plurality of positions.

8. The method of claim 3, wherein the step of positioning the optical pen at the position comprises positioning the optical pen off center in the hole such that at least three spectral peak components in the spectral intensity profile are isolated spectral peak components respectively corresponding to the distances from the optical pen to the interior surface along the at least three measurement directions.

9. The method of claim 1, wherein the step of positioning the optical pen at the position comprises positioning the optical pen at a first off center position in the hole such that at least a first spectral peak component in the spectral intensity profile is an isolated spectral peak component corresponding to a unique distance from the optical pen to the interior surface along a corresponding unique measurement direction at the first off center position.

10. The method of claim 9, wherein:
the optical pen is coupled to a coordinate measuring machine (CMM), and the CMM is used to position the optical pen;
the method comprises repeating the positioning, receiving, and operating steps corresponding to second and third off center positions such that at least second and third isolated spectral peak components in second and third spectral intensity profiles are isolated spectral peak components respectively corresponding to unique distances from the optical pen to the interior surface along corresponding unique measurement directions at the second and third off center positions; and
in the step of determining the geometric characteristic the signal processing operations comprise:
a) analyzing at least the first, second and third spectral intensity profiles to determine at least first, second and third distance measurements from the optical pen to the interior surface along the corresponding unique measurement directions at the first, second and third off center positions, and
b) determining the geometric characteristic of the hole based on at least the first, second and third distance measurements and CMM coordinates respectively corresponding to the first, second and third off center positions.

11. The method of claim 10, wherein the hole has a circular cross-section having a radius r, and the optical pen is configured such that its measuring range along each of the at least three measurement directions extends at most a distance RMAX' from its center Z axis, wherein RMAX'<r.

12. The method of claim 1, wherein:
the interior surface of the hole comprises screw threads;
the optical pen is coupled to a coordinate measuring machine (CMM), and the CMM is used to position the optical pen;
the step of positioning the optical pen at the position comprises positioning the optical pen at a current position, which corresponds to an axial position along a direction parallel to a central axis of the hole and a current off center position transverse to the central axis of the hole, such that at least a first spectral peak component in the corresponding spectral intensity profile is an isolated spectral peak component corresponding to a unique distance from the optical pen to the interior surface along a corresponding unique measurement direction at the current position;

the method comprises repeating the positioning, receiving, and operating steps at a plurality of different current positions that correspond to a plurality of different axial positions; and in the step of determining the geometric characteristic the signal processing operations comprise:
a) analyzing a plurality of spectral intensity profiles, respectively corresponding to the plurality of different current positions corresponding to the plurality of different axial positions, to determine a plurality of distance measurements from the optical pen to the screw threads along a corresponding unique measurement direction at the plurality of different current positions that correspond to the plurality of different axial positions, and
b) determining the geometric characteristic of the screw threads based on at least some of the plurality of distance measurements at the plurality of different current positions that correspond to the plurality of different axial positions.

13. The method of claim 12, wherein determining the geometric characteristic of the screw threads is further based on CMM coordinates that characterize at least some of the plurality of different current positions.

14. The method of claim 1, wherein the optical pen is coupled to a coordinate measuring machine (CMM), and a CMM controller is used to control position and movement of the optical pen.

15. The method of claim 1, wherein the beam dividing deflecting element includes one of a pyramid shaped reflective optical element comprising at least three planar reflective facets corresponding to the at least three measurement directions, or a cone-shaped reflective optical element.

16. A chromatic confocal point sensor (CPS) system for inspecting a geometric characteristic of a hole at least partially surrounded by an interior surface, the CPS system comprising:
an optical pen comprising a housing that extends along a central Z axis of the optical pen, a confocal aperture that outputs source light, an axial chromatic aberration portion arranged to input the source light and output measurement light that is focused with axial chromatic aberration, and a beam dividing deflecting element arranged to distribute the measurement light simultaneously along at least three measurement directions transverse to the central Z axis;
an electronics portion comprising a source light generating portion, a spectrometer, and a signal processor, wherein the electronics portion is configured such that:
when the optical pen is positioned at a position inside the hole, the electronics portion operates such that the measurement light is incident on the interior surface along the at least three measurement directions, and the spectrometer receives the measurement light reflected from the at least three measurement directions back through the confocal aperture of the optical pen at the position;
the signal processor operates in conjunction with the spectrometer to obtain a spectral intensity profile of the measurement light, the spectral intensity profile comprising spectral peak components corresponding to distances to the interior surface that are within the optical pen's measuring range along the at least three measurement directions; and
the signal processor performs the operations comprising at least one of a), b) and c) which respectively comprise:
a) determining the geometric characteristic of the hole based at least partially on signal processing operations comprising analyzing the spectral intensity profile to determine at least a first distance measurement from the optical pen to the interior surface along at least a first measurement direction;
b) analyzing the spectral intensity profile to determine at least a first distance measurement from the optical pen to the interior surface along at least a first measurement direction, and outputting the at least first distance measurement to an external system configured to determine the geometric characteristic of the hole based at least partially on the at least first distance measurement; and
c) outputting the spectral intensity profile to an external system configured to determine the geometric characteristic of the hole based at least partially on signal processing operations comprising analyzing the spectral intensity profile to determine at least a first distance measurement from the optical pen to the interior surface along at least a first measurement direction.

17. The chromatic confocal point sensor system of claim 16, wherein the beam dividing deflecting element includes one of a pyramid shaped reflective optical element comprising at least three planar reflective facets corresponding to the at least three measurement directions, or a cone-shaped reflective optical element.

18. The chromatic confocal point sensor system of claim 17, wherein the beam dividing deflecting element comprises a pyramid shaped reflective optical element including at most four planar reflective faces corresponding to at most four measurement directions.

19. The chromatic confocal point sensor system of claim 16, wherein the external system comprises a coordinate measuring machine (CMM) to which the optical pen is coupled, wherein the CMM is configured to control position and movement of the optical pen.

20. The chromatic confocal point sensor system of claim 19, wherein the CMM is configured to:
automatically position the optical pen at the position inside a hole located on a workpiece to be inspected by the CMM, wherein the position is a predetermined position defined in a part program executed by the CMM; and
determine the geometric characteristic of the hole based at least partially on the at least first distance measurement in combination with CMM coordinates corresponding to the predetermined position.

* * * * *